US005837458A

United States Patent [19]
Minshull et al.

[11] Patent Number: 5,837,458
[45] Date of Patent: *Nov. 17, 1998

[54] METHODS AND COMPOSITIONS FOR CELLULAR AND METABOLIC ENGINEERING

[75] Inventors: Jeremy Minshull, San Francisco; Willem P. C. Stemmer, Los Gatos, both of Calif.

[73] Assignee: Maxygen, Inc., Santa Clara, Calif.

[*] Notice: The term of this patent shall not extend beyond the expiration date of Pat. No. 5,605,793.

[21] Appl. No.: 650,400

[22] Filed: May 20, 1996

Related U.S. Application Data

[63] Continuation-in-part of Ser. No. 198,431, Feb. 17, 1994, which is a continuation-in-part of PCT/US95/02126 Feb. 17, 1995 Pat. No. 5,605,793, Ser. No. 537,874, Mar. 4, 1996, Ser. No. 621,859, Mar. 25, 1996, Ser. No. 621,430, Mar. 25, 1996, abandoned, and Ser. No. 425,684, Apr. 18, 1995.

[51] Int. Cl.$^6$ .............................. C12Q 1/68; C12N 15/00
[52] U.S. Cl. ............................. 435/6; 435/172.1; 935/76; 935/77; 935/78
[58] Field of Search .......................... 435/6, 91.2, 172.3; 935/76, 77, 78

[56] References Cited

U.S. PATENT DOCUMENTS

| | | | |
|---|---|---|---|
| 4,994,368 | 2/1991 | Goodman et al. | 435/6 |
| 5,032,514 | 7/1991 | Anderson et al. | 435/138 |
| 5,043,272 | 8/1991 | Hartley | 435/91 |
| 5,093,257 | 3/1992 | Gray | 435/202 |
| 5,223,408 | 6/1993 | Goeddel et al. | 435/69.3 |
| 5,279,952 | 1/1994 | Wu | 435/172.3 |
| 5,356,801 | 10/1994 | Rambosek et al. | 435/195 |
| 5,360,728 | 11/1994 | Prasher | 435/189 |
| 5,541,309 | 7/1996 | Prasher | 536/23.2 |
| 5,652,116 | 7/1997 | Grandi et al. | 435/69.1 |

FOREIGN PATENT DOCUMENTS

| | | |
|---|---|---|
| 0 252666 B1 | 1/1988 | European Pat. Off. . |
| WO 90/07576 | 7/1990 | WIPO . |
| WO 91/01087 | 2/1991 | WIPO . |
| WO 95/17413 | 6/1995 | WIPO . |
| WO95/22625 | 8/1995 | WIPO . |
| WO 97/07205 | 2/1997 | WIPO . |

OTHER PUBLICATIONS

Appleyard, V.C.L. et al., "Secondary metabolite production in filamentous fungi displayed," *Mol. Gen. Gent.* 247:338–342 (1995).
Arkin et al., "An Algorithm for Protein Engineering: Simulations of Recursive Ensemble Mutagenesis" *Proc. Natl. Acad. Sci. USA* 89:7811–7815 (1992).
Armstrong, G.A., "Eubacteria Show Their Tru Colors: Genetics of Carotenoid Pigment Biosynthesis from Microbes to Plants," *J. Bacteriol.* 176(16):4795–4802 (1994).
Arnold, F.H., "Protein engineering for unusual environments," *Cr. Opin. Biotechnol.* 4:450–455 (1993).

Backman, K. et al., "Genetic Engineering of Metabolic Pathways Applied to the Production of Phenylalanine," *Ann. NY Acad. Sci.* 589:16–24 (1990).
Bailey, J.E., "Toward a Science of Metabolic Engineering," *Science* 252:1668–1675 (1991).
Beaudry et al., "Directed Evolution of an RNA Enzyme" *Science* 257:635–641 (1992).
Berger et al., "Phoenix Mutagenesis: One–Step Reassembly of Multiply Cleaved Plasmids with Mixtures of Mutant and Wild–Type Fragments" Anal. Biochem. 214:571–579 see pp. 571–578 (1993).
Berkhout et al., "In Vivo Selection of Randomly Mutated Retroviral Genomes" Nucleic Acids Research 21:5020–5023 No. 22 (1993).
Botella, J.A. et al., "A cluster of structural and regulatory genes for light–induced carotenogenesis in *Myxococcus xanthus*," *Eur. J. Biochem.* 233:238–248 (1995).
Boudrant, J., "Microbial processes for ascorbic acid biosynthesis: a review," *Enzyme Microb. Technol.* 12:322–329 (1990).
Brenner, V. et al., "Genetic construction of PCB degraders," *Biodegradation* 5:359–377 (1994).
Bryant, C. et al., "Cloning, Nucleotide Sequence, and Expression of the Nitroreductases Gene from *Enterobacter Cloacae*," *J. Biol. Chem.* 266(7):4126–4130 (1991).
Cadwell et al., "Randomization of Genes by PCR Mutagenesis" PCR Methods and Applications 2:28–33 (1992).
Cameron, D.C. et al., "Cellular and Metabolic Engineering," *Applied Biochem. Biotech.* 38:105–140 (1993).
Chakrabarty, A.M., "Microbial Degradation of Toxic Chemicals: Evolutionary Insights and Practical Considerations," *Am. Soc. Micro. Biol. News* 62:130–137 (1996).
Chater, K.F., "The improving prospects for yield increase by genetic engineering in antibiotic–producing streptomycetes," *Bio/Technology* 8:115–121 (1990).
Chen, C.W. et al., "Cloning and Expression of a DNA sequence conferring cepamycin C production," *Bio/Technology* 6:1222–1224 (1988).
Chen, K. et al., "Tuning the activity of an enzyme for unusual environments: Sequential random mutagenesis of subtilisin E for catalysis in dimethylformamide," *Proc. Natl. Acad. Sci. U.S.A.* 90:5168–5622 (1993).
Calogero Sabina et al., "In Vivo Recombination and the Production of Hybrid Genes," *Microbiology letters,* 1992, vol. 97, pp. 41–44.

(List continued on next page.)

Primary Examiner—W. Gary Jones
Assistant Examiner—Ethan Whisenant
Attorney, Agent, or Firm—Townsend & Townsend & Crew

[57] ABSTRACT

The present invention is generally directed to the evolution of new metabolic pathways and the enhancement of bioprocessing through a process herein termed recursive sequence recombination. Recursive sequence recombination entails performing iterative cycles of recombination and screening or selection to "evolve" individual genes, whole plasmids or viruses, multigene clusters, or even whole genomes. Such techniques do not require the extensive analysis and computation required by conventional methods for metabolic engineering.

36 Claims, 1 Drawing Sheet

OTHER PUBLICATIONS

Caren Robert et al., "Efficient Sampling of Protein Sequence Space for Multiple Mutants," *Biotechnology,* May 12, 1994, vol. 12, pp. 517–520.

Dacre, J.C., "Nonspecificity of the Gibbs Reaction," *Anal. Chem.* 43(4):589–591 (1971).

Denome, S.A. et al., "Dibenzothiophene and Naphtalene in Pseudomonas Strains: Complete DNA Sequence of an Upper Naphthalene Catholic Pathway," *J. Bacteriol.* 175(21):6890–6901 (1993).

de Souza, M.L. et al., "Cloning, Characterization, and Expressing of a Gene Region from Pseudomonas sp. Strain ADP Involved in the Dechlorination of Atrazine," *Appl. Environ. Micro.* 61(9):3373–3378 (1995).

Delagrave Simon et al., "Recursive Ensemble Mutagenesis," *Protein Engineering,* 1993, vol. 6, No. 3, pp. 327–331.

Eaton, R.W. et al., "Formation of Indigo and Related Compounds from Indolecarboxylic Acids by Aromatic Acid–Degrading Bacteria: Chromogenic Reactions for Cloning Genes Encoding Dioxygenases That Act on Aromatic Acids," *J. Bacteriol.* 177(23):6983–6988 (1995).

Erickson B.D. et al., "Enhanced Biodegradation of Polychlorinated Biphenyls after Site–Directed Mutagenesis of a Biphenyl Dioxygenase Gene," *App. Environ. Micro.* 59(11):3858–3862 (1993).

Evnin, L.B. et al., "Substrate specificity of trypsin inestigated by using a genetic selection," *Proc. Natl. Acad. Sci. U.S.A.* 87:6659–6663 (1990).

Fernandez–Lafuente R. et al., "Additional stabilization of penicillin G acylase–agarose derivatives by controlled chemical modification with formaldehyde," *Enzyme Microb. Technol.* 14:489–495 (1992).

Ford, T. et al., "Metal–microbe interactions," *Bioextraction and Biodeterioration of Metals,* pp. 1–23.

Furukawa K. et al., "Gene–specific transposon mutagenesis of the biphenyl/polychlorinated biphenyl–degradation–controlling bph operon in soil bacteria," *Gene* 98:21–28 (1991).

Furukawa K. et al., Gene Components Responsible for Discrete Substrate Specificity in the Metabolism of Biphenyl (bph Operon) and Toluene (tod Operon), *J. Bact.* 175(16):5224–5232 (1993).

Furukawa K. et al., "Efficient Degradation of Trichloroethylene by a Hybrid Aromatic Ring Dioxygenase," *J. Bacteriol.* 176(7):2121–2123 (1994).

Goguen, B. et al., "Clonogenic cytotoxicity testing by microdrop encapsulation," *Nature* 363:189–190 (1995).

Hart, H.E. et al., "Scintillation proximity assay (SPA)—a new method of immunoassay," *Mol. Immunol.* 16:265–267 (1979).

Hassan, H.M. et al., "Intracellular Producton of Superoxide Radical and Hydrogen Peroxide by Redox Active Compounds," *Arch. Bioch. Biop.* 196(2):385–395 (1979).

Hayase N. et al., "*Pseudomonas putida* KF715 bphABCD Operon Encoding Biphenyl and Polychlorinated Biphenyl Degradation: Cloning, Analysis, and Expression in Soil Bacteria," *J. Bacteriol.* 172(2):1160–1164 (1990).

Hermes et al., "Searching Sequence Space by Definably Random Mutagenesis: Improving the Catalytic Potency of an Enzyme" *Proc. Natl. Acad. Sci. USA* 87:696–700 (1990).

Heim et al., "*Wavelength Mutations and Posttranslational Autoxidation of Green Fluorescent Protein,*" *Proc. Natl. Acad. Sci. USA* 501–12504 (1994).

Hofer, B. et al., "The biphenyl/polychlorinated biphenyl–degradation locus (bph) of Pseudomonas sp. LB400 encodes four additional metabolic enzymes," *Gene* 144:9–16 (1994).

Hopwood, D.A., "Antibiotics: opportunities for genetic manipulation," *Phil. Trans. R. Soc. Lond.* B324:549–562 (1989).

Hoshino T. et al., "Molecular Cloning and Sequence Analysis of the crtB Gene of *Thermus Thermophilus* HB27, an Extreme Thermophile Producing Carotenoid Pigments," *Appl. Environ. Micro.* 59(9):3150–3153 (1993).

Hunter, C.N. et al., "Introduction of New Carotenoids into the Bacterial Photosynthetic Apparatus by Combining the Carotenoid Biosynthetic Pathways of *Erwinia herbicola* and *Rhodobacter sphaeroides,*" *J. Bacteriol.* 176(12):3692–3697 (1994).

Hutchinson, C.R., "Prospects for the Discovery of New (Hybrid) Antibiotics by Genetic Engineering of Antibiotic–Producing Bacteria," *Med. Res. Rev.* 8(4):557–567 (1988).

Hutchinson, C.R. et al., "Drug Development through the Genetic Engineering of Antibiotic–Producing Microorganisms," *Ann. NY Acad. Sci.* 656:78–93 (1991).

Hutchinson, C.R., "Drug Synthesis by Genetically Engineered Microorganisms," *Bio/Technology* 12:375–308 (1994).

Ji, G. et al., "Bacterial resistance mechanisms for heavy metals of environmental convern," *J. Ind. Micro.* 14:61–75 (1995).

Jones et al., "Recombinant Circle PCR and Recombinant PCR for Site–Specific Mutagenesis Without PCR Product Purification," *BioTechniques* 12(4) : pp. 528–534 (1992).

Kim et al., "Human Immunodeficiency Virus Reverse Transcriptase" The Journal of Biological Chemistry 271, No. 9 pp. 4872–4878 (1996).

Kajiwara, S. et al., "Isolation and functional identification of a novel cDNA for astaxanthin biosynthesis from *Heamtococcus pluvialis*, and astaxanthin synthesis in *Escherichia coli,*" *Plant Mol. Bio.* 29:343–352 (1995).

Kato, F. et al., "Carotenoid synthesis in *Streptomyces setonii* ISP5395 is induced by the gene crtS, whose product is similar to a sigma factor," *Mol. Gen. Genet.* 247:387–390 (1995).

Kellog, S.T. et al., "Plasmid Assisted Molecular Breeding: New Technique for Enhanced Biodegradation of Persistent Toxic Chemicals," *Science* 214:1133–1135 (1981).

Kleinkauf, H. et al., "A nonribosomal system of peptide biosynthesis," *Eur. J. Biochem.* 236:335–351 (1996).

Krawiec, S., "Bacterial desulfurization of thiophenes: screening techniques and some speculations regarding the biochemical and genetic bases," *Devl. Indust. Microbiol.* 31:103–114 (1990).

Lang, H.P. et al., "Complete DNA Sequence, Specific Tn5 Insertion Map, and Gene Assignment of the Carotenoid Biosynthesis Pathway of *Rhodobacter sphaeroides,*" *J. Bacteriol.* 177(8):2064–2073 (1995).

Leung et al., "A Method for Random Mutagensis of a Defined DNA Segment Using a Modified Polymerase Chain Reaction" 1:11–15, see pp. 11–14 (1989).

Liao, J.C., "Modelling and analysis of metabolic pathways," *Curr. Opin. Biotech.* 4:211–216 (1993).

Mandelbaum, R.T. et al., "Isolation and Characterization of a Pseudomonas sp. That Mineralizes the s–Triazine Herbicide Atrazine," *Appl. Environ. Micro.* 61(4):1451–1457 (1995).

Marks James et al., "By–Passing Immunization: Building High Affinity Human Antibodies by Chain Shuffling" Bio/Technology 10:779–782 (1992).

Marrs, B., "Mobilization of the Genes for Photosynthesis from *Rhodopseudomonas capsulata* by a Promiscuous Plasmid," *J. Bacteriol.* 146(3):1003–1012 (1981).

Martin, L. et al., "Cloning and sequencing of the pac gene encoding he penicillin G acylase of *Bacillus megaterium* ATCC 14945," *FEMS Microbiol. Lett.* 125:287–292 (1995).

Matthysse, A.G. et al., "Genes Required for Cellulose Synthesis in *Agrobacterium tumefaciens*," *J. Bacteriol.* 177(4):1069–1075 (1995).

McDaniel, R. et al., "Engineered Biosynthesis of Novel Polyketides," *Science* 262:1546–1550 (1995).

Meyerhans Andreas et al., "DNA Recombination during PCR," *Nucleic Acids Research*, 1990, vol. 18, No. 7, pp. 1687–1691.

Misawa, N. et al., "Structure and Functional Analysis of a Marine Bacterial Carotenoid biosynthesis Gene Cluster and Astaxanthin Biosynthetic Pathway Proposed at the Gene Level," *J. Bacteriol.* 177(22):6576–6584 (1995).

Moore, J.C. et al., "Directed evolution of a para–nitrobenzyl esterase for aqueous–organic solvents," *Nature Biotechnology* 14:458–467 (1996).

Murdock, D. et al., "Construction of Metabolic Operons Catalyzing the De Novo Biosynthesis of Indigo in *Escherichia coli*," *Bio/Technology* 11:381–386 (1993).

Nisbet, L.J. et al., "Developments in Microbial Products Screening," *Ann. Rep. Med. Chem.* 21:149–157 (1986).

Oliphant et al., "Cloning of Random–Sequence Oligodeoxynucleotides" *Gene* 44:177–183 (1988).

Omura, S., "Philosophy of new Drug Discovery," *Microbio. Rev.* 50(3):259–279 (1986).

Paau, A.S., "Improvement of Rhizogium Inoclulants by Mutation, Genetic Engineering and Formulation," *Biotech. Adv.* 9:173–184 (1991).

Piepersberg, W., Pathway Engineering in Secondary Metabolite–Producing Actinomycetes, *Crit. Rev. Biotechnol.* 14:251–285 (1994).

Poirier, Y. et al., "Polyhydroxybutyrate, a Biodegradable Thermoplastic, Produced in Transgenic Plants," *Science* 256:520–523 (1992).

Pompon Denis et al., "Protein Engineering by cDNA Recombination in Yeasts: Shuffling of Mamalian Cytochrome P–450 Functions," *Gene*, 1989, vol. 83, pp. 15–24.

Powell, K.T. et al., "Gel microdroplets and flow cytometry: Rapid determination of antibody secretion by individual cells within a cell population," *Bio/Technology* 8:333–337 (1990).

Rawlings, D.E. et al., "Mining with Microbes," *Bio/Technology* 13:773–778 (1995).

Rees, W.D. et al., "A molecular biological approach to reducing dietary amino acid needs," *Bio/Technology* 8:629–633 (1990).

Reidhaar–Olson et al., "Combinatorial Cassette Mutagenesis as a Probe of the Informational Content of Protein Sequences" Science 241:53–57 (1988).

Roa et al, Recombination and Polymerase Error Facilitate Restoration of Infectivity in Brome Mosaic Virus Journal of Virology No. 2 67:969–979 (1993).

Sanseverino, J. et al., "Plasmid–Mediated Mineralization of Naphthalene, Phenanthrene, Anthracene," *Applied Environ. Micro.* 59(6):1931–1937 (1993).

Sarthy, A.V et al., "Expression of the *Escherichia coli* Xylose Isomerase Gene in *Saccharomyces cerevisiae*," *Appl. Envinron. Micro.* 53(9):1996–2000 (1987).

Scherrer, S. et al., "Periplasmic aggregation limits the proteolytic maturation of the *Eschericia coli* Penicillin G amidase presursor polypeptide," *Appl. Microbiol. Biotechnol.* 42:85–91 (1994).

Selifonova, O.V. et al., "Use of and ibp–lux Fusion To Study Regulation of the Isopropylbenzene Catabolism Operon of *Pseudomonas putida* RE204 and To Detect Hydrophobic Pollutants in the Environment," *Appl. Environ. Microbiol.* 62(3):778–783 (1986).

Silver, S. et al., "Newer Systems for Bacterial Resistances to Toxic Heavy Metals," *Environ. Health Perspect.* 102:107–113 (1994).

Simon, M.J. et al., "Sequences of genes encoding naphthalene dioxygenase in *Pseudomonas putida* strains G7 and NCIB 9816–4," *Gene* 127:31–37 (1993).

Simpson, T.W. et al., "Two paradigms of metabolic engineering applied to amino acid biosynthesis," *Biochem. Soc. Trans.* 23:381–387 (1995).

Smith, D.J. et al., "Cloning and heterologous expression of the penicillin biosynthesis gene closuter from *penicillium chrysogenum*," *Bio/Technology* 8:39–41 (1990).

Steele, D.B. et al., "Techniques for selection of industrially important microorganisms," *Ann. Rev. Microbiol.* 45:89–106 (1991).

Stemmer, W.P.C., "Rapid Evolution of a Protein In Vitro by DNA Shuffling," *Nature* 370:389–391 (1994).

Stemmer, W.P.C., "DNA Shuffling by Random Fragmentation and Reassembly: In Vitro Recombination for Molecular Evolution," *Proc. Natl. Acad. Sci. U.S.A.* 91:10747–10751 (1994).

Stemmer et al., "Selection of an Active Single Chain FV Antibody from a Protein Linker Library Prepared by Enzymatic Inverse PCR" Biotechniques 14:256–265 (1992).

Stephanopoulos, G. et al., "Metabolic engineering—methodologies and future prospects," *Trends. Biotech.* 11:392–396 (1993).

Stephanopoulos, G., "Metabolic engineering," *Curr. Opin. Biotech.* 5:196–200 (1994).

Tabata, K. et al., "A carotenogenic gene cluster exists on a large plasmid in *Thermus thermopilus*," *FEBS Letts.* 341:251–255 (1994).

Timmis, K.N. et al., "Designing microorganisms for the Treatment of Toxic Wastes," *Ann. Rev. Microbiol.* 48:525–557 (1994).

Wackett, L.P. et al., "Metabolism of polyhalogenated compounds by a genetically engineered bacterium," *Nature* 368:627–629 (1994).

Wang et al., "Identification of Glial Filament Protein and Vimentin in the Same Intermediate Filament System in Human Glioma Cells," *Proc. Natl. Sci. USA* 81(7):2102–2106 (Abstract only, 1984).

Wang, Y et al., "Nucleotide Sequence of a Chomosomal Mercury Resistance Determinant from a Bacillus sp. With Broad–Spectrum Mercury Resistance," *J. Bacteriol.* 171(1):83–92 (1989).

Weber, H. et al., "Formation of Genes Coding for Hybrid Proteins by Recombinant Between Related, Cloned Genes in *E. Coli*," *Nucleic Acids Research* 11(16):5661–5669 (1983).

Weaver, J. C. et al., "Microdrop Technology: A General Method for Separating Cells by Function and Composition," *Methods* 2:234–247 (1991).

Wehmeier, U.F., "New multifunctional *Eschericia coli–Streptomyces* shuttle vectors allowing blue–white screening on Xgal plates," *Gene* 165:149–150 (1995).

Zhao, X., "EPD, a novel technology for drug delivery," *Adv. Drug Delivery Rev.* 17:257–262 (1995).

Zukowski, M.M. et al., "Chromogenic identification of genetic regulatory signals in *Bacilus subtilis* based on expression of a cloned Pseudomonas gene," *Proc. Natl. Acad. Sci. U.S.A.* 80:1101–1105 (1983).

Zylstra, G.J. et al., "Cloning and Analysis of the Genes for Polycyclic Aromatic Hydrocarbon Degradation," *Ann. NY Acad. Sci.* 721:386–398 (1994).

Dieffenbach et al., *PCR Primer, A Laboratory Manual,* New York, Cold Spring Harbor Press, pp. 581–621 (1995).

Higuchi, R., "Using PCT to Engineer DNA," *PCR Technology,* Erlich, H.A., ed., New York, Stockton Press, pp. 61–70 (1989).

Prasher, Trends in Genetics 11(8):320–323 (Aug. 1995).

Andersson, D. et al., "Muller's Ratchet Decreases Fitness of a DNA–based Microbe," *Proc. Natl. Acad. Sci. U.S.A.* 93:906–907 (1996).

Barrett, M. et al., "Genotypic Analysis of Multiple Loci in Somatic Cells by Whole Genome Amplification," *Nucleic Acids Research* 23:3488–3492 (1995).

Crameri, A. et al., "Improved Green Fluorescent Protein by Molecular Evolution Using DNA Shuffling," *Nature Biotechnology* 14:315–319 (1996).

Crameri, A. et al., "Construction and Evolution of Antibody–phage Libraries by DNA Shuffling," *Nature Medicine* 2:100–300 (1996).

Feinberg, A. et al., "A Technique for Radiolabeling DNA Restriction Endonuclease Fragments to High Specific Activity," *Analytical Biochemistry* 132:6–13 (1983).

Ho, S. et al., "Site–directed Mutagenesis by Overlap Extension Using the Polymerase Chain Reaction," *Gene* 77:51–59 (1989).

Horton, R. et al., "Engineering Hybrid Genes Without the Use of Restriction Enzymes: Gene Splicing by Overlap Extension," *Gene* 77:61–68 (1989).

Levichkin, I.V. et al., "A New Approach to Construction of Hybrid Genes: Homolog Recombination Method," *Molecular Biology* 29:572–577 (1995).

Pharmacia Catalog, "Recombinant Phage Antibody System: Mouse ScFv Module Expression Module Detection Module," pp. 70–71, 1993 Edition.

Ramos, J.L. et al., "The Behavior of Bacteria Designed for Biodegradation," *Bio/Technology* 12:1349–1355 (1994).

Stemmer, W.P.C. et al., "Single–Step Assembly of a Gene and Entire Plasmid from Large Numbers of Oligodeoxyribonucleotides," *Gene* 164:49–53 (1995).

Stemmer, W.P.C., "Searching Sequence Space: Using Recombination to Search More Efficiently and Thoroughly Instead of Making Bigger Combinatorial Libraries," *Bio/Technology* 13:539–553 (1995).

Stemmer, W.P.C., "Rapid Evolution of a Protein In Vitro by DNA Shuffling," *Nature* 370:389–391 (1994).

Stemmer, W.P.C., "The Evolution of Molecular Computation," *Science* 270:1510 (1995).

Stemmer, W.P.C., "DNA Shuffling by Random Fragmentation and Reassembly: In Vitro Recombination for Molecular Evolution," *Proc. Natl. Acad. Sci. U.S.A.* 91:10747–10751 (1994).

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AGCGCCCAAT ACGCAAACCG CCTCTCCCCG CGCGTTGGCC 40

(2) INFORMATION FOR SEQ ID NO:2:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

CTATGCGGCA TCAGAGCAGA TTGTACTGAG AGTGCACCAT 40

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CAGGACTTAT CGCCACTGGC AGC 23

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CTCGCTCTGC TAATCCTGTT ACC 23

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GCATATTATG AGCGTTTAGG CTTAATTCC 29

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CGGTATCCTT TTTCCGTACG TTC 23

(2) INFORMATION FOR SEQ ID NO:7:

-continued (i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:7:

GTTGAAGAGG TGAAGAAAGT TCTCC                                         25

(2) INFORMATION FOR SEQ ID NO:8:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:8:

GTTCGTCGAT TTCCACGCTT GGC                                           23

(2) INFORMATION FOR SEQ ID NO:9:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:9:

AGGGCCTCGT GATACGCCTA TT                                            22

(2) INFORMATION FOR SEQ ID NO:10:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:10:

ACGAAAACTC ACGTTAAGGG ATT                                           23

METHODS AND COMPOSITIONS FOR CELLULAR AND METABOLIC ENGINEERING

This application is a continuation-in-part of U.S. patent application Ser. No. 08/198,431, filed Feb. 17, 1994, now U.S. Pat. No. 5,605,793, Ser. No. PCT/US95/02126, filed, Feb. 17, 1995, Ser. No. 08/537,874, filed Mar. 4, 1996, Ser. No. 08/621,859, filed Mar. 25, 1996, Ser. No. 08/621,430, filed Mar. 25, 1996, now abandoned and Ser. No. 08/425,684, filed Apr. 18, 1995, the specifications of which are herein incorporated by reference in their entirety for all purposes.

BACKGROUND OF THE INVENTION

Metabolic engineering is the manipulation of intermediary metabolism through the use of both classical genetics and genetic engineering techniques. Cellular engineering is generally a more inclusive term referring to the modification of cellular properties. Cameron et al. (*Applied Biochem. Biotech.* 38:105–140 (1993)) provide a summary of equivalent terms to describe this type of engineering, including "metabolic engineering", which is most often used in the context of industrial microbiology and bioprocess engineering, "in vitro evolution" or "directed evolution", most often used in the context of environmental microbiology, "molecular breeding", most often used by Japanese researchers, "cellular engineering", which is used to describe modifications of bacteria, animal, and plant cells, "rational strain development", and "metabolic pathway evolution". In this application, the terms "metabolic engineering" and "cellular engineering" are used preferentially for clarity; the term "evolved" genes is used as discussed below.

Metabolic engineering can be divided into two basic categories: modification of genes endogenous to the host organism to alter metabolite flux and introduction of foreign genes into an organism. Such introduction can create new metabolic pathways leading to modified cell properties including but not limited to synthesis of known compounds not normally made by the host cell, production of novel compounds (e.g. polymers, antibiotics, etc.) and the ability to utilize new nutrient sources. Specific applications of metabolic engineering can include the production of specialty and novel chemicals, including antibiotics, extension of the range of substrates used for growth and product formation, the production of new catabolic activities in an organism for toxic chemical degradation, and modification of cell properties such as resistance to salt and other environmental factors.

Bailey (*Science* 252:1668–1674 (1991)) describes the application of metabolic engineering to the recruitment of heterologous genes for the improvement of a strain, with the caveat that such introduction can result in new compounds that may subsequently undergo further reactions, or that expression of a heterologous protein can result in proteolysis, improper folding, improper modification, or unsuitable intracellular location of the protein, or lack of access to required substrates. Bailey recommends careful configuration of a desired genetic change with minimal perturbation of the host.

Liao (*Curr. Opin. Biotech.* 4:211–216 (1993)) reviews mathematical modelling and analysis of metabolic pathways, pointing out that in many cases the kinetic parameters of enzymes are unavailable or inaccurate.

Stephanopoulos et al. (*Trends. Biotechnol.* 11:392–396 (1993)) describe attempts to improve productivity of cellular systems or effect radical alteration of the flux through primary metabolic pathways as having difficulty in that control architectures at key branch points have evolved to resist flux changes. They conclude that identification and characterization of these metabolic nodes is a prerequisite to rational metabolic engineering. Similarly, Stephanopoulos (*Curr. Opin. Biotech.* 5:196–200 (1994)) concludes that rather than modifying the "rate limiting step" in metabolic engineering, it is necessary to systematically elucidate the control architecture of bioreaction networks.

The present invention is generally directed to the evolution of new metabolic pathways and the enhancement of bioprocessing through a process herein termed recursive sequence recombination. Recursive sequence recombination entails performing iterative cycles of recombination and screening or selection to "evolve" individual genes, whole plasmids or viruses, multigene clusters, or even whole genomes (Stemmer, *Bio/Technology* 13:549–553 (1995)). Such techniques do not require the extensive analysis and computation required by conventional methods for metabolic engineering. Recursive sequence recombination allows the recombination of large numbers of mutations in a minimum number of selection cycles, in contrast to traditional, pairwise recombination events.

Thus, because metabolic and cellular engineering can pose the particular problem of the interaction of many gene products and regulatory mechanisms, recursive sequence recombination (RSR) techniques provide particular advantages in that they provide recombination between mutations in any or all of these, thereby providing a very fast way of exploring the manner in which different combinations of mutations can affect a desired result, whether that result is increased yield of a metabolite, altered catalytic activity or substrate specificity of an enzyme or an entire metabolic pathway, or altered response of a cell to its environment.

SUMMARY OF THE INVENTION

One aspect of the invention is a method of evolving a biocatalytic activity of a cell, comprising:

(a) recombining at least a first and second DNA segment from at least one gene conferring ability to catalyze a reaction of interest, the segments differing from each other in at least two nucleotides, to produce a library of recombinant genes;

(b) screening at least one recombinant gene from the library that confers enhanced ability to catalyze the reaction of interest by the cell relative to a wildtype form of the gene;

(c) recombining at least a segment from at least one recombinant gene with a further DNA segment from at least one gene, the same or different from the first and second segments, to produce a further library of recombinant genes;

(d) screening at least one further recombinant gene from the further library of recombinant genes that confers enhanced ability to catalyze the reaction of interest in the cell relative to a previous recombinant gene;

(e) repeating (c) and (d), as necessary, until the further recombinant gene confers a desired level of enhanced ability to catalyze the reaction of interest by the cell.

Another aspect of the invention is a method of evolving a gene to confer ability to catalyze a reaction of interest, the method comprising:

(1) recombining at least first and second DNA segments from at least one gene conferring ability to catalyze a reaction of interest, the segments differing from each other in at least two nucleotides, to produce a library of recombinant genes;

(2) screening at least one recombinant gene from the library that confers enhanced ability to catalyze a reaction of interest relative to a wildtype form of the gene;

(3) recombining at least a segment from the at least one recombinant gene with a further DNA segment from the at least one gene, the same or different from the first and second segments, to produce a further library of recombinant genes;

(4) screening at least one further recombinant gene from the further library of recombinant genes that confers enhanced ability to catalyze a reaction of interest relative to a previous recombinant gene;

(5) repeating (3) and (4), as necessary, until the further recombinant gene confers a desired level of enhanced ability to catalyze a reaction of interest.

A further aspect of the invention is a method of generating a new biocatalytic activity in a cell, comprising:

(1) recombining at least first and second DNA segments from at least one gene conferring ability to catalyze a first reaction related to a second reaction of interest, the segments differing from each other in at least two nucleotides, to produce a library of recombinant genes;

(2) screening at least one recombinant gene from the library that confers a new ability to catalyze the second reaction of interest;

(3) recombining at least a segment from at least one recombinant gene with a further DNA segment from the at least one gene, the same or different from the first and second segments, to produce a further library of recombinant genes;

(4) screening at least one further recombinant gene from the further library of recombinant genes that confers enhanced ability to catalyze the second reaction of interest in the cell relative to a previous recombinant gene;

(5) repeating (3) and (4), as necessary, until the further recombinant gene confers a desired level of enhanced ability to catalyze the second reaction of interest in the cell.

Another aspect of the invention is a modified form of a cell, wherein the modification comprises a metabolic pathway evolved by recursive sequence recombination.

A further aspect of the invention is a method of optimizing expression of a gene product, the method comprising:

(1) recombining at least first and second DNA segments from at least one gene conferring ability to produce the gene product, the segments differing from each other in at least two nucleotides, to produce a library of recombinant genes;

(2) screening at least one recombinant gene from the library that confers optimized expression of the gene product relative to a wildtype form of the gene;

(3) recombining at least a segment from the at least one recombinant gene with a further DNA segment from the at least one gene, the same or different from the first and second segments, to produce a further library of recombinant genes;

(4) screening at least one further recombinant gene from the further library of recombinant genes that confers optimized ability to produce the gene product relative to a previous recombinant gene;

(5) repeating (3) and (4), as necessary, until the further recombinant gene confers a desired level of optimized ability to express the gene product.

A further aspect of the invention is a method of evolving a biosensor for a compound A of interest, the method comprising:

(1) recombining at least first and second DNA segments from at least one gene conferring ability to detect a related compound B, the segments differing from each other in at least two nucleotides, to produce a library of recombinant genes;

(2) screening at least one recombinant gene from the library that confers optimized ability to detect compound A relative to a wildtype form of the gene;

(3) recombining at least a segment from the at least one recombinant gene with a further DNA segment from the at least one gene, the same or different from the first and second segments, to produce a further library of recombinant genes;

(4) screening at least one further recombinant gene from the further library of recombinant genes that confers optimized ability to detect compound A relative to a previous recombinant gene;

(5) repeating (3) and (4), as necessary, until the further recombinant gene confers a desired level of optimized ability to detect compound A.

DESCRIPTION OF THE SPECIFIC EMBODIMENTS

Figure 1:
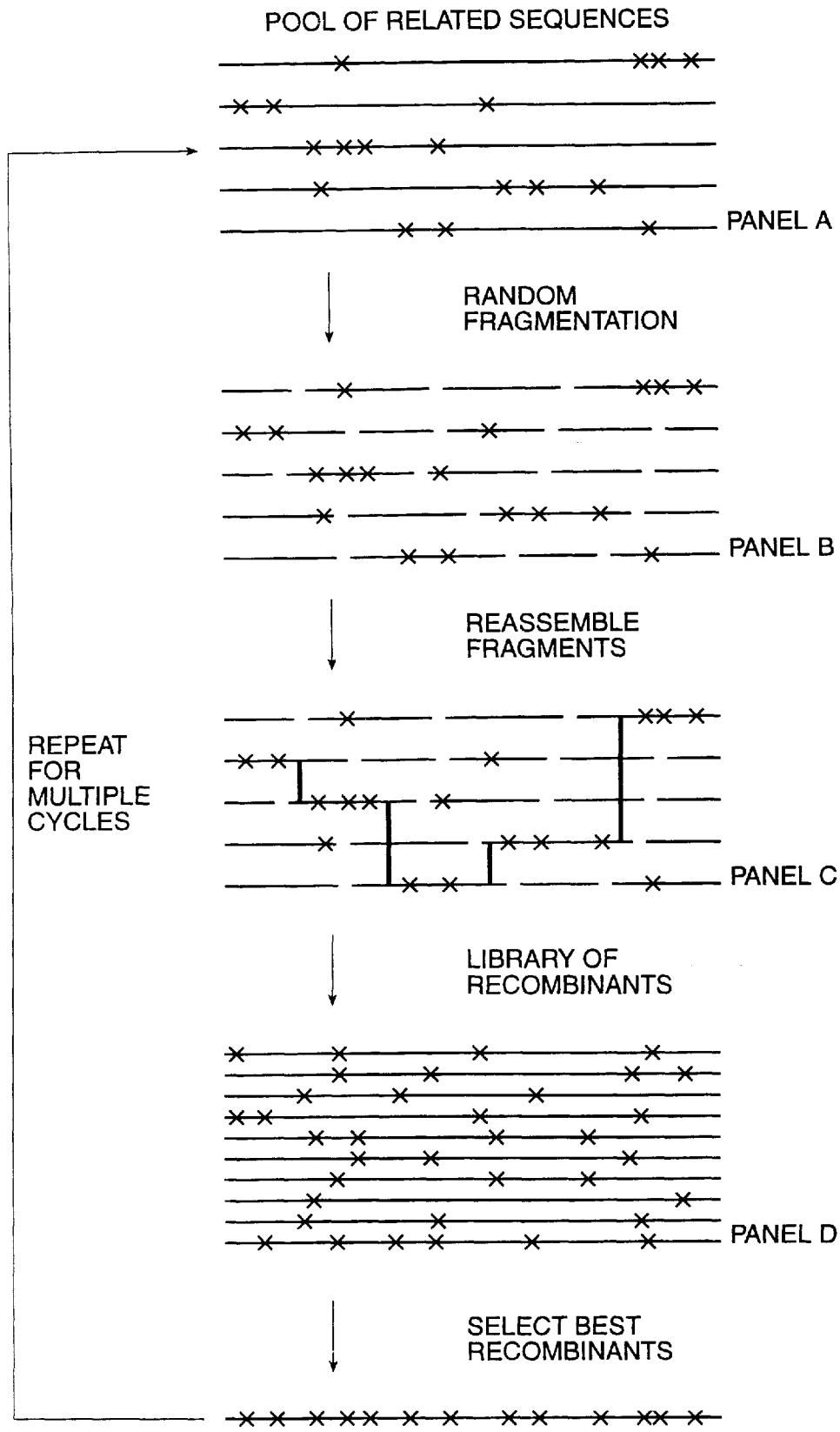
FIG. 1 is a drawing depicting a scheme for in vitro recursive sequence recombination.

The invention provides a number of strategies for evolving metabolic and bioprocessing pathways through the technique of recursive sequence recombination. One strategy entails evolving genes that confer the ability to use a particular substrate of interest as a nutrient source in one species to confer either more efficient use of that substrate in that species, or comparable or more efficient use of that substrate in a second species. Another strategy entails evolving genes that confer the ability to detoxify a compound of interest in one or more species of organisms. Another strategy entails evolving new metabolic pathways by evolving an enzyme or metabolic pathway for biosynthesis or degradation of a compound A related to a compound B for the ability to biosynthesize or degrade compound B, either in the host of origin or a new host. A further strategy entails evolving a gene or metabolic pathway for more efficient or optimized expression of a particular metabolite or gene product. A further strategy entails evolving a host/vector system for expression of a desired heterologous product. These strategies may involve using all the genes in a multi-step pathway, one or several genes, genes from different organisms, or one or more fragments of a gene.

The strategies generally entail evolution of gene(s) or segment(s) thereof to allow retention of function in a heterologous cell or improvement of function in a homologous or heterologous cell. Evolution is effected generally by a process termed recursive sequence recombination. Recursive sequence recombination can be achieved in many different formats and permutations of formats, as described in further detail below. These formats share some common principles. Recursive sequence recombination entails successive cycles of recombination to generate molecular diversity, i.e., the creation of a family of nucleic acid molecules showing substantial sequence identity to each other but differing in the presence of mutations. Each recombination cycle is followed by at least one cycle of screening or selection for molecules having a desired characteristic. The molecule(s) selected in one round form the starting materials for generating diversity in the next round. In any given cycle, recombination can occur in vivo or in vitro. Furthermore, diversity resulting from recombination can be augmented in any cycle by applying prior methods of mutagenesis (e.g., error-prone PCR or cassette mutagenesis, passage through bacterial mutator strains, treatment with chemical mutagens) to either the substrates for or products of recombination.

I. Formats for Recursive Sequence Recombination

Some formats and examples for recursive sequence recombination, sometimes referred to as DNA shuffling or molecular breeding, have been described by the present inventors and co-workers in co-pending applications, U.S. patent application Ser. Nos. 08/621,430, filed Mar. 25, 1996; PCT/US95/02126, filed Feb. 17, 1995; 08/621,859, filed Mar. 25, 1996; 08/198,431, filed Feb. 17, 1994; Stemmer, *Science* 270:1510 (1995); Stemmer et al., *Gene* 164:49–53 (1995); Stemmer, *Bio/Technology* 13:549–553 (1995); Stemmer, *Proc. Natl. Acad. Sci. U.S.A.* 91:10747–10751 (1994); Stemmer, *Nature* 370:389–391 (1994); Crameri et al. *Nature Medicine* 2(1):1–3 (1996); Crameri et al. *Nature Biotechnology* 14:315–319 (1996), each of which is incorporated by reference in its entirety for all purposes.

(1) In Vitro Formats

One format for recursive sequence recombination in vitro is illustrated in FIG. 1. The initial substrates for recombination are a pool of related sequences. The X's in FIG. 1, panel A, show where the sequences diverge. The sequences can be DNA or RNA and can be of various lengths depending on the size of the gene or DNA fragment to be recombined or reassembled. Preferably the sequences are from 50 bp to 100 kb.

The pool of related substrates can be fragmented, usually at random, into fragments of from about 5 bp to 5 kb or more, as shown in FIG. 1, panel B. Preferably the size of the random fragments is from about 10 bp to 1000 bp, more preferably the size of the DNA fragments is from about 20 bp to 500 bp. The substrates can be digested by a number of different methods, such as DNAseI or RNAse digestion, random shearing or restriction enzyme digestion. The concentration of nucleic acid fragments of a particular length or sequence is often less than 0.1% or 1% by weight of the total nucleic acid. The number of different specific nucleic acid fragments in the mixture is usually at least about 100, 500 or 1000.

The mixed population of nucleic acid fragments are denatured by heating to about 80° C. to 100° C., more preferably from 90° C. to 96° C., to form single-stranded nucleic acid fragments and then reannealed. Single-stranded nucleic acid fragments having regions of sequence identity with other single-stranded nucleic acid fragments can then be reannealed by cooling to 20° C. to 75° C., and preferably from 40° C. to 65° C. Renaturation can be accelerated by the addition of polyethylene glycol ("PEG") or salt. The salt concentration is preferably from 0 mM to 600 mM, more preferably the salt concentration is from 10 mM to 100 mM. The salt may be such salts as $(NH_4)_2SO_4$, KCl, or NaCl. The concentration of PEG is preferably from 0% to 20%, more preferably from 5% to 10%. The fragments that reanneal can be from different substrates as shown in FIG. 1, panel C.

The annealed nucleic acid fragments are incubated in the presence of a nucleic acid polymerase, such as Taq or Klenow, and dNTP's (i.e. DATP, dCTP, dGTP and dTTP). If regions of sequence identity are large, Taq or other high-temperature polymerase can be used with an annealing temperature of between 45°–65° C. If the areas of identity are small, Klenow or other low-temperature polymerases can be used with an annealing temperature of between 20°–30° C. The polymerase can be added to the random nucleic acid fragments prior to annealing, simultaneously with annealing or after annealing.

The cycle of denaturation, renaturation and incubation of random nucleic acid fragments in the presence of polymerase is sometimes referred to as "shuffling" of the nucleic acid in vitro. This cycle is repeated for a desired number of times. Preferably the cycle is repeated from 2 to 100 times, more preferably the sequence is repeated from 10 to 40 times. The resulting nucleic acids are a family of double-stranded polynucleotides of from about 50 bp to about 100 kb, preferably from 500 bp to 50 kb, as shown in FIG. 1, panel D. The population represents variants of the starting substrates showing substantial sequence identity thereto but also diverging at several positions. The population has many more members than the starting substrates. The population of fragments resulting from recombination is preferably first amplified by PCR, then cloned into an appropriate vector and the ligation mixture used to transform host cells.

In a variation of in vitro shuffling, subsequences of recombination substrates can be generated by amplifying the full-length sequences under conditions which produce a substantial fraction, typically at least 20 percent or more, of incompletely extended amplification products. The amplification products, including the incompletely extended amplification products are denatured and subjected to at least one additional cycle of reannealing and amplification. This variation, wherein at least one cycle of reannealing and amplification provides a substantial fraction of incompletely extended products, is termed "stuttering." In the subsequent amplification round, the incompletely extended products anneal to and prime extension on different sequence-related template species.

In a further variation, at least one cycle of amplification can be conducted using a collection of overlapping single-stranded DNA fragments of related sequence, and different lengths. Each fragment can hybridize to and prime polynucleotide chain extension of a second fragment from the collection, thus forming sequence-recombined polynucleotides. In a further variation, single-stranded DNA fragments of variable length can be generated from a single primer by Vent DNA polymerase on a first DNA template. The single stranded DNA fragments are used as primers for a second, Kunkel-type template, consisting of a uracil-containing circular single-stranded DNA. This results in multiple substitutions of the first template into the second (see Levichkin et al. *Mol. Biology* 29:572–577 (1995)).

Gene clusters such as those involved in polyketide synthesis (or indeed any multi-enzyme pathways catalyzing analogous metabolic reactions) can be recombined by recursive sequence recombination even if they lack DNA sequence homology. Homology can be introduced using synthetic oligonucleotides as PCR primers. In addition to the specific sequences for the gene being amplified, all of the primers used to amplify one type of enzyme (for example the acyl carrier protein in polyketide synthesis) are synthesized to contain an additional sequence of 20–40 bases 5' to the gene (sequence A) and a different 20–40 base sequence 3' to the gene (sequence B). The adjacent gene (in this case the keto-synthase) is amplified using a 5' primer which contains the complementary strand of sequence B (sequence B'), and a 3' primer containing a different 20–40 base sequence (C). Similarly, primers for the next adjacent gene (keto-reductases) contain sequences C' (complementary to C) and D. If 5 different polyketide gene clusters are being shuffled, all five acyl carrier proteins are flanked by sequences A and B following their PCR amplification. In this way, small regions of homology are introduced, making the gene clusters into site-specific recombination cassettes. Subsequent to the initial amplification of individual genes, the amplified genes can then be mixed and subjected to primerless PCR. Sequence B at the 3' end of all of the five acyl carrier protein genes can anneal with and prime DNA synthesis from sequence B' at the 5' end of all five keto reductase genes. In this way all possible combinations of genes within the cluster can be obtained. Oligonucleotides allow such recombinants to be obtained in the absence of sufficient sequence homology for recursive sequence recombination described above. Only homology of function is required to produce functional gene clusters.

This method is also useful for exploring permutations of any other multi-subunit enzymes. An example of such enzymes composed of multiple polypeptides that have shown novel functions when the subunits are combined in novel ways are dioxygenases. Directed recombination between the four protein subunits of biphenyl and toluene dioxygenases produced functional dioxygenases with increased activity against trichloroethylene (Furukawa et. al. *J. Bacteriol.* 176: 2121–2123 (1994)). This combination of subunits from the two dioxygenases could also have been produced by cassette-shuffling of the dioxygenases as described above, followed by selection for degradation of trichloroethylene.

In some polyketide synthases, the separate functions of the acyl carrier protein, keto-synthase, keto-reductase, etc. reside in a single polypeptide. In these cases domains within the single polypeptide may be shuffled, even if sufficient homology does not exist naturally, by introducing regions of homology as described above for entire genes. In this case, it may not be possible to introduce additional flanking sequences to the domains, due to the constraint of maintaining a continuous open reading frame. Instead, groups of oligonucleotides are synthesized that are homologous to the 3' end of the first domain encoded by one of the genes to be shuffled, and the 5' ends of the second domains encoded by all of the other genes to be shuffled together. This is repeated with all domains, thus providing sequences that allow recombination between protein domains while maintaining their order.

The cassette-based recombination method can be combined with recursive sequence recombination by including gene fragments (generated by DNase, physical shearing, DNA stuttering, etc.) for one or more of the genes. Thus, in addition to different combinations of entire genes within a cluster (e.g., for polyketide synthesis), individual genes can be shuffled at the same time (e.g., all acyl carrier protein genes can also be provided as fragmented DNA), allowing a more thorough search of sequence space.

(2) In Vivo Formats (a) Plasmid-Plasmid Recombination

The initial substrates for recombination are a collection of polynucleotides comprising variant forms of a gene. The variant forms usually show substantial sequence identity to each other sufficient to allow homologous recombination between substrates. The diversity between the polynucleotides can be natural (e.g., allelic or species variants), induced (e.g., error-prone PCR or error-prone recursive sequence recombination), or the result of in vitro recombination. Diversity can also result from resynthesizing genes encoding natural proteins with alternative codon usage. There should be at least sufficient diversity between substrates that recombination can generate more diverse products than there are starting materials. There must be at least two substrates differing in at least two positions. However, commonly a library of substrates of $10^3$–$10^8$ members is employed. The degree of diversity depends on the length of the substrate being recombined and the extent of the functional change to be evolved. Diversity at between 0.1–25% of positions is typical. The diverse substrates are incorporated into plasmids. The plasmids are often standard cloning vectors, e.g., bacterial multicopy plasmids. However, in some methods to be described below, the plasmids include mobilization (MOB) functions. The substrates can be incorporated into the same or different plasmids. Often at least two different types of plasmid having different types of selectable markers are used to allow selection for cells containing at least two types of vector. Also, where different types of plasmid are employed, the different plasmids can come from two distinct incompatibility groups to allow stable co-existence of two different plasmids within the cell. Nevertheless, plasmids from the same incompatibility group can still co-exist within the same cell for sufficient time to allow homologous recombination to occur.

Plasmids containing diverse substrates are initially introduced into cells by any method (e.g., chemical transformation, natural competence, electroporation, biolistics, packaging into phage or viral systems). Often, the plasmids are present at or near saturating concentration (with respect to maximum transfection capacity) to increase the probability of more than one plasmid entering the same cell. The plasmids containing the various substrates can be transfected simultaneously or in multiple rounds. For example, in the latter approach cells can be transfected with a first aliquot of plasmid, transfectants selected and propagated, and then infected with a second aliquot of plasmid.

Having introduced the plasmids into cells, recombination between substrates to generate recombinant genes occurs within cells containing multiple different plasmids merely by propagating the cells. However, cells that receive only one plasmid are unable to participate in recombination and the potential contribution of substrates on such plasmids to evolution is not fully exploited (although these plasmids may contribute to some extent if they are progagated in mutator ccells). The rate of evolution can be increased by allowing all substrates to participate in recombination. Such can be achieved by subjecting transfected cells to electroporation. The conditions for electroporation are the same as those conventionally used for introducing exogenous DNA into cells (e.g., 1,000–2,500 volts, 400 $\mu$F and a 1–2 mM gap). Under these conditions, plasmids are exchanged between cells allowing all substrates to participate in recombination. In addition the products of recombination can undergo further rounds of recombination with each other or with the original substrate. The rate of evolution can also be increased by use of conjugative transfer. To exploit conjugative transfer, substrates can be cloned into plasmids having MOB genes, and tra genes are also provided in cis or in trans to the MOB genes. The effect of conjugative transfer is very similar to electroporation in that it allows plasmids to move between cells and allows recombination between any substrate and the products of previous recombination to occur, merely by propagating the culture. The rate of evolution can also be increased by fusing cells to induce exchange of plasmids or chromosomes. Fusion can be induced by chemical agents, such as PEG, or viral proteins, such as influenza virus hemagglutinin, HSV-1 gB and gD. The rate of evolution can also be increased by use of mutator host cells (e.g., Mut L, S, D, T, H in bacteria and Ataxia telangiectasia human cell lines).

The time for which cells are propagated and recombination is allowed to occur, of course, varies with the cell type but is generally not critical, because even a small degree of recombination can substantially increase diversity relative to the starting materials. Cells bearing plasmids containing recombined genes are subject to screening or selection for a desired function. For example, if the substrate being evolved contains a drug resistance gene, one would select for drug resistance. Cells surviving screening or selection can be subjected to one or more rounds of screening/selection followed by recombination or can be subjected directly to an additional round of recombination.

The next round of recombination can be achieved by several different formats independently of the previous round. For example, a further round of recombination can be effected simply by resuming the electroporation or conjugation-mediated intercellular transfer of plasmids described above. Alternatively, a fresh substrate or substrates, the same or different from previous substrates, can be transfected into cells surviving selection/screening. Optionally, the new substrates are included in plasmid vectors bearing a different selective marker and/or from a different incompatibility group than the original plasmids. As a further alternative, cells surviving selection/screening can be subdivided into two subpopulations, and plasmid DNA from one subpopulation transfected into the other, where the substrates from the plasmids from the two subpopulations undergo a further round of recombination. In either of the latter two options, the rate of evolution can be increased by employing DNA extraction, electroporation, conjugation or mutator cells, as described above. In a still further variation, DNA from cells surviving screening/selection can be extracted and subjected to in vitro recursive sequence recombination.

After the second round of recombination, a second round of screening/selection is performed, preferably under conditions of increased stringency. If desired, further rounds of recombination and selection/screening can be performed using the same strategy as for the second round. With successive rounds of recombination and selection/screening, the surviving recombed substrates evolve toward acquisition of a desired phenotype. Typically, in this and other methods of recursive recombination, the final product of recombination that has acquired the desired phenotype differs from starting substrates at 0.1%–25% of positions and has evolved at a rate orders of magnitude in excess (e.g., by at least 10-fold, 100-fold, 1000-fold, or 10,000 fold) of the rate of naturally acquired mutation of about 1 mutation per $10^{-9}$ positions per generation (see Anderson et al. *Proc. Natl. Acad. Sci. U.S.A.* 93:906–907 (1996)). The "final product" may be transferred to another host more desirable for utilization of the "shuffled" DNA. This is particularly advantageous in situations where the more desirable host is less efficient as a host for the many cycles of mutation/recombination due to the lack of molecular biology or genetic tools available for other organisms such as *E. coli*.

(b) Virus-Plasmid Recombination

The strategy used for plasmid-plasmid recombination can also be used for virus-plasmid recombination; usually, phage-plasmid recombination. However, some additional comments particular to the use of viruses are appropriate. The initial substrates for recombination are cloned into both plasmid and viral vectors. It is usually not critical which substrate(s) are inserted into the viral vector and which into the plasmid, although usually the viral vector should contain different substrate(s) from the plasmid. As before, the plasmid (and the virus) typically contains a selective marker.

The plasmid and viral vectors can both be introduced into cells by transfection as described above. However, a more efficient procedure is to transfect the cells with plasmid, select transfectants and infect the transfectants with virus. Because the efficiency of infection of many viruses approaches 100% of cells, most cells transfected and infected by this route contain both a plasmid and virus bearing different substrates.

Homologous recombination occurs between plasmid and virus generating both recombined plasmids and recombined virus. For some viruses, such as filamentous phage, in which intracellular DNA exists in both double-stranded and single-stranded forms, both can participate in recombination. Provided that the virus is not one that rapidly kills cells, recombination can be augmented by use of electroporation or conjugation to transfer plasmids between cells. Recombination can also be augmented for some types of virus by allowing the progeny virus from one cell to reinfect other cells. For some types of virus, virus infected-cells show resistance to superinfection. However, such resistance can be overcome by infecting at high multiplicity and/or using mutant strains of the virus in which resistance to superinfection is reduced.

The result of infecting plasmid-containing cells with virus depends on the nature of the virus. Some viruses, such as filamentous phage, stably exist with a plasmid in the cell and also extrude progeny phage from the cell. Other viruses, such as lambda having a cosmid genome, stably exist in a cell like plasmids without producing progeny virions. Other viruses, such as the T-phage and lytic lambda, undergo recombination with the plasmid but ultimately kill the host cell and destroy plasmid DNA. For viruses that infect cells without killing the host, cells containing recombinant plasmids and virus can be screened/selected using the same approach as for plasmid-plasmid recombination. Progeny virus extruded by cells surviving selection/screening can also be collected and used as substrates in subsequent rounds of recombination. For viruses that kill their host cells, recombinant genes resulting from recombination reside only in the progeny virus. If the screening or selective assay requires expression of recombinant genes in a cell, the recombinant genes should be transferred from the progeny virus to another vector, e.g., a plasmid vector, and retransfected into cells before selection/screening is performed.

For filamentous phage, the products of recombination are present in both cells surviving recombination and in phage extruded from these cells. The dual source of recombinant products provides some additional options relative to the plasmid-plasmid recombination. For example, DNA can be isolated from phage particles for use in a round of in vitro recombination. Alternatively, the progeny phage can be used to transfect or infect cells surviving a previous round of screening/selection, or fresh cells transfected with fresh substrates for recombination.

(c) Virus-Virus Recombination

The principles described for plasmid-plasmid and plasmid-viral recombination can be applied to virus-virus recombination with a few modifications. The initial substrates for recombination are cloned into a viral vector. Usually, the same vector is used for all substrates. Preferably, the virus is one that, naturally or as a result of mutation, does not kill cells. After insertion, some viral genomes can be packaged in vitro or using a packaging cell line. The packaged viruses are used to infect cells at high multiplicity such that there is a high probability that a cell will receive multiple viruses bearing different substrates.

After the initial round of infection, subsequent steps depend on the nature of infection as discussed in the previous section. For example, if the viruses have phagemid genomes such as lambda cosmids or M13, F1 or Fd phagemids, the phagemids behave as plasmids within the cell and undergo recombination simply by propagating the cells. Recombination is particularly efficient between single-stranded forms of intracellular DNA. Recombination can be augmented by electroporation of cells.

Following selection/screening, cosmids containing recombinant genes can be recovered from surviving cells, e.g., by heat induction of a cos⁻ lysogenic host cell, or extraction of DNA by standard procedures, followed by repackaging cosmid DNA in vitro.

If the viruses are filamentous phage, recombination of replicating form DNA occurs by propagating the culture of infected cells. Selection/screening identifies colonies of cells containing viral vectors having recombinant genes with improved properties, together with phage extruded from such cells. Subsequent options are essentially the same as for plasmid-viral recombination.

(d) Chromosome Recombination

This format can be used to especially evolve chromosomal substrates. The format is particularly useful in situations in which many chromosomal genes contribute to a phenotype or one does not know the exact location of the chromosomal gene(s) to be evolved. The initial substrates for recombination are cloned into a plasmid vector. If the chromosomal gene(s) to be evolved are known, the substrates constitute a family of sequences showing a high degree of sequence identity but some divergence from the chromosomal gene. If the chromosomal genes to be evolved have not been located, the initial substrates usually constitute a library of DNA segments of which only a small number show sequence identity to the gene or gene(s) to be evolved. Divergence between plasmid-borne substrate and the chromosomal gene(s) can be induced by mutagenesis or by obtaining the plasmid-borne substrates from a different species than that of the cells bearing the chromosome.

The plasmids bearing substrates for recombination are transfected into cells having chromosomal gene(s) to be evolved. Evolution can occur simply by propagating the culture, and can be accelerated by transferring plasmids between cells by conjugation or electroporation. Evolution can be further accelerated by use of mutator host cells or by seeding a culture of nonmutator host cells being evolved with mutator host cells and inducing intercellular transfer of plasmids by electroporation or conjugation. Preferably, mutator host cells used for seeding contain a negative selectable marker to facilitate isolation of a pure culture of the nonmutator cells being evolved. Selection/screening identifies cells bearing chromosomes and/or plasmids that have evolved toward acquisition of a desired function.

Subsequent rounds of recombination and selection/screening proceed in similar fashion to those described for plasmid-plasmid recombination. For example, further recombination can be effected by propagating cells surviving recombination in combination with electroporation or conjugative transfer of plasmids. Alternatively, plasmids bearing additional substrates for recombination can be introduced into the surviving cells. Preferably, such plasmids are from a different incompatibility group and bear a different selective marker than the original plasmids to allow selection for cells containing at least two different plasmids. As a further alternative, plasmid and/or chromosomal DNA can be isolated from a subpopulation of surviving cells and transfected into a second subpopulation. Chromosomal DNA can be cloned into a plasmid vector before transfection.

(e) Virus-Chromosome Recombination

As in the other methods described above, the virus is usually one that does not kill the cells, and is often a phage or phagemid. The procedure is substantially the same as for plasmid-chromosome recombination. Substrates for recombination are cloned into the vector. Vectors including the substrates can then be transfected into cells or in vitro packaged and introduced into cells by infection. Viral genomes recombine with host chromosomes merely by propagating a culture. Evolution can be accelerated by allowing intercellular transfer of viral genomes by electroporation, or reinfection of cells by progeny virions. Screening/selection identifies cells having chromosomes and/or viral genomes that have evolved toward acquisition of a desired function.

There are several options for subsequent rounds of recombination. For example, viral genomes can be transferred between cells surviving selection/recombination by electroporation. Alternatively, viruses extruded from cells surviving selection/screening can be pooled and used to superinfect the cells at high multiplicity. Alternatively, fresh substrates for recombination can be introduced into the cells, either on plasmid or viral vectors.

II. Recursive Sequence Recombination Techniques for Metabolic and Cellular Engineering A. Starting Materials Thus, a general method for recursive sequence recombination for the embodiments herein is to begin with a gene encoding an enzyme or enzyme subunit and to evolve that gene either for ability to act on a new substrate, or for enhanced catalytic properties with an old substrate, either alone or in combination with other genes in a multistep pathway. The term "gene" is used herein broadly to refer to any segment or sequence of DNA associated with a biological function. Genes can be obtained from a variety of sources, including cloning from a source of interest or synthesizing from known or predicted sequence information, and may include sequences designed to have desired parameters. The ability to use a new substrate can be assayed in some instances by the ability to grow on a substrate as a nutrient source. In other circumstances such ability can be assayed by decreased toxicity of a substrate for a host cell, hence allowing the host to grow in the presence of that substrate. Biosynthesis of new compounds, such as antibiotics, can be assayed similarly by growth of an indicator organism in the presence of the host expressing the evolved genes. For example, when an indicator organism used in an overlay of the host expressing the evolved gene(s), wherein the indicator organism is sensitive or expected to be sensitive to the desired antibiotic, growth of the indicator organism would be inhibited in a zone around the host cell or colony expressing the evolved gene(s).

Another method of identifying new compounds is the use of standard analytical techniques such as mass spectroscopy, nuclear magnetic resonance, high performance liquid chromatography, etc. Recombinant microorganisms can be pooled and extracts or media supernatants assayed from these pools. Any positive pool can then be subdivided and the procedure repeated until the single positive is identified ("sib-selection").

In some instances, the starting material for recursive sequence recombination is a discrete gene, cluster of genes, or family of genes known or thought to be associated with metabolism of a particular class of substrates.

One of the advantages of the instant invention is that structural information is not required to estimate which parts of a sequence should be mutated to produce a functional hybrid enzyme.

In some embodiments of the invention, an initial screening of enzyme activities in a particular assay can be useful in identifying candidate enzymes as starting materials. For example, high throughput screening can be used to screen enzymes for dioxygenase-type activities using aromatic acids as substrates. Dioxygenases typically transform indole-2-carboxylate and indole-3-carboxylate to colored products, including indigo (Eaton et. al. *J. Bacteriol.* 177:6983–6988 (1995)). DNA encoding enzymes that give some activity in the initial assay can then be recombined by the recursive techniques of the invention and rescreened. The use of such initial screening for candidate enzymes against a desired target molecule or analog of the target molecule can be especially useful to generate enzymes that catalyze reactions of interest such as catabolism of man-made pollutants.

The starting material can also be a segment of such a gene or cluster that is recombined in isolation of its surrounding DNA, but is relinked to its surrounding DNA before screening/selection of recombination products. In other instances, the starting material for recombination is a larger segment of DNA that includes a coding sequence or other locus associated with metabolism of a particular substrate at an unknown location. For example, the starting material can be a chromosome, episome, YAC, cosmid, or phage P1 clone. In still other instances, the starting material is the whole genome of an organism that is known to have desirable metabolic properties, but for which no information localizing the genes associated with these characteristics is available.

In general any type of cells can be used as a recipient of evolved genes. Cells of particular interest include many bacterial cell types, both gram-negative and gram-positive, such as Rhodococcus, Streptomycetes, Actinomycetes, Corynebacteria, Penicillium, Bacillus, *Escherichia coli*, Pseudomonas, Salmonella, and Erwinia. Cells of interest also include eukaryotic cells, particularly mammalian cells (e.g., mouse, hamster, primate, human), both cell lines and primary cultures. Such cells include stem cells, including embryonic stem cells, zygotes, fibroblasts, lymphocytes, Chinese hamster ovary (CHO), mouse fibroblasts (NIH3T3), kidney, liver, muscle, and skin cells. Other eukaryotic cells of interest include plant cells, such as maize, rice, wheat, cotton, soybean, sugarcane, tobacco, and arabidopsis; fish, algae, fungi (Penicillium, Fusarium, Aspergillus, Podospora, Neurospora), insects, yeasts (Picchia and Saccharomyces).

The choice of host will depend on a number of factors, depending on the intended use of the engineered host, including pathogenicity, substrate range, environmental hardiness, presence of key intermediates, ease of genetic manipulation, and likelihood of promiscuous transfer of genetic information to other organisms. Particularly advantageous hosts are *E. coli*, lactobacilli, Streptomycetes, Actinomycetes and filamentous fungi.

The breeding procedure starts with at least two substrates, which generally show substantial sequence identity to each other (i.e., at least about 50%, 70%, 80% or 90% sequence identity) but differ from each other at certain positions. The difference can be any type of mutation, for example, substitutions, insertions and deletions. Often, different segments differ from each other in perhaps 5–20 positions. For recombination to generate increased diversity relative to the starting materials, the starting materials must differ from each other in at least two nucleotide positions. That is, if there are only two substrates, there should be at least two divergent positions. If there are three substrates, for example, one substrate can differ from the second as a single position, and the second can differ from the third at a different single position. The starting DNA segments can be natural variants of each other, for example, allelic or species variants. The segments can also be from nonallelic genes showing some degree of structural and usually functional relatedness (e.g., different genes within a superfamily such as the immunoglobulin superfamily). The starting DNA segments can also be induced variants of each other. For example, one DNA segment can be produced by error-prone PCR replication of the other, or by substitution of a mutagenic cassette. Induced mutants can also be prepared by propagating one (or both) of the segments in a mutagenic strain. In these situations, strictly speaking, the second DNA segment is not a single segment but a large family of related segments. The different segments forming the starting materials are often the same length or substantially the same length. However, this need not be the case; for example; one segment can be a subsequence of another. The segments can be present as part of larger molecules, such as vectors, or can be in isolated form.

The starting DNA segments are recombined by any of the recursive sequence recombination formats described above to generate a diverse library of recombinant DNA segments. Such a library can vary widely in size from having fewer than 10 to more than $10^5$, $10^7$, or $10^9$ members. In general, the starting segments and the recombinant libraries generated include full-length coding sequences and any essential regulatory sequences, such as a promoter and polyadenylation sequence, required for expression. However, if this is not the case, the recombinant DNA segments in the library can be inserted into a common vector providing the missing sequences before performing screening/selection.

If the recursive sequence recombination format employed is an in vivo format, the library of recombinant DNA segments generated already exists in a cell, which is usually the cell type in which expression of the enzyme with altered substrate specificity is desired. If recursive sequence recombination is performed in vitro, the recombinant library is preferably introduced into the desired cell type before screening/selection. The members of the recombinant library can be linked to an episome or virus before introduction or can be introduced directly. In some embodiments of the invention, the library is amplified in a first host, and is then recovered from that host and introduced to a second host more amenable to expression, selection, or screening, or any other desirable parameter. The manner in which the library is introduced into the cell type depends on the DNA-uptake characteristics of the cell type, e.g., having viral receptors, being capable of conjugation, or being naturally competent. If the cell type is insusceptible to natural and chemical-induced competence, but susceptible to electroporation, one would usually employ electroporation. If the cell type is insusceptible to electroporation as well, one can employ biolistics. The biolistic PDS-1000 Gene Gun (Biorad, Hercules, Calif.) uses helium pressure to accelerate DNA-coated gold or tungsten microcarriers toward target cells. The process is applicable to a wide range of tissues, including plants, bacteria, fungi, algae, intact animal tissues, tissue culture cells, and animal embryos. One can employ electronic pulse delivery, which is essentially a mild electroporation format for live tissues in animals and patients. Zhao, *Advanced Drug Delivery Reviews* 17:257–262 (1995). Novel methods for making cells competent are described in co-pending application U.S. patent application Ser. No. 08/621,430, filed Mar. 25, 1996. After introduction of the library of recombinant DNA genes, the cells are optionally propagated to allow expression of genes to occur.

B. Selection and Screening

Screening is, in general, a two-step process in which one first determines which cells do and do not express a screening marker and then physically separates the cells having the desired property. Selection is a form of screening in which identification and physical separation are achieved simultaneously, for example, by expression of a selectable marker, which, in some genetic circumstances, allows cells expressing the marker to survive while other cells die (or vice versa). Screening markers include, for example, luciferase, β-galactosidase, and green fluorescent protein. Screening can also be done by observing such aspects of growth as colony size, halo formation, etc. Additionally, screening for production of a desired compound, such as a therapeutic drug or "designer chemical" can be accomplished by observing binding of cell products to a receptor or ligand, such as on a solid support or on a column. Such screening can additionally be accomplished by binding to antibodies, as in an ELISA. In some instances the screening process is preferably automated so as to allow screening of suitable numbers of colonies or cells. Some examples of automated screening devices include fluorescence activated cell sorting, especially in conjunction with cells immobilized in agarose (see Powell et. al. *Bio/Technology* 8:333–337 (1990); Weaver et. al. *Methods* 2:234–247 (1991)), automated ELISA assays, etc. Selectable markers can include, for example, drug, toxin resistance, or nutrient synthesis genes. Selection is also done by such techniques as growth on a toxic substrate to select for hosts having the ability to detoxify a substrate, growth on a new nutrient source to select for hosts having the ability to utilize that nutrient source, competitive growth in culture based on ability to utilize a nutrient source, etc.

In particular, uncloned but differentially expressed proteins (e.g., those induced in response to new compounds, such as biodegradable pollutants in the medium) can be screened by differential display (Appleyard et al. *Mol. Gen. Gent.* 247:338–342 (1995)). Hopwood (*Phil Trans R. Soc. Lond* B 324:549–562) provides a review of screens for antibiotic production. Omura (*Microbio. Rev.* 50:259–279 (1986) and Nisbet (*Ann Rep. Med. Chem.* 21:149–157 (1986)) disclose screens for antimicrobial agents, including supersensitive bacteria, detection of β-lactamase and D,D-carboxypeptidase inhibition, β-lactamase induction, chromogenic substrates and monoclonal antibody screens. Antibiotic targets can also be used as screening targets in high throughput screening. Antifungals are typically screened by inhibition of fungal growth. Pharmacological agents can be identified as enzyme inhibitors using plates containing the enzyme and a chromogenic substrate, or by automated receptor assays. Hydrolytic enzymes (e.g., proteases, amylases) can be screened by including the substrate in an agar plate and scoring for a hydrolytic clear zone or by using a colorimetric indicator (Steele et al. *Ann. Rev. Microbiol.* 45:89–106 (1991)). This can be coupled with the use of stains to detect the effects of enzyme action (such as congo red to detect the extent of degradation of celluloses and hemicelluloses). Tagged substrates can also be used. For example, lipases and esterases can be screened using different lengths of fatty acids linked to umbelliferyl. The action of lipases or esterases removes this tag from the fatty acid, resulting in a quenching of umbelliferyl fluorescence. These enzymes can be screened in microtiter plates by a robotic device.

Fluorescence activated cell sorting (FACS) methods are also a powerful tool for selection/screening. In some instances a fluorescent molecule is made within a cell (e.g., green fluorescent protein). The cells producing the protein can simply be sorted by FACS. Gel microdrop technology allows screening of cells encapsulated in agarose microdrops (Weaver et al. *Methods* 2:234–247 (1991)). In this technique products secreted by the cell (such as antibodies or antigens) are immobilized with the cell that generated them. Sorting and collection of the drops containing the desired product thus also collects the cells that made the product, and provides a ready source for the cloning of the genes encoding the desired functions. Desired products can be detected by incubating the encapsulated cells with fluorescent antibodies (Powell et al. *Bio/Technology* 8:333–337 (1990)). FACS sorting can also be used by this technique to assay resistance to toxic compounds and antibiotics by selecting droplets that contain multiple cells (i.e., the product of continued division in the presence of a cytotoxic compound; Goguen et al. *Nature* 363:189–190 (1995)). This method can select for any enzyme that can change the fluorescence of a substrate that can be immobilized in the agarose droplet.

In some embodiments of the invention, screening can be accomplished by assaying reactivity with a reporter molecule reactive with a desired feature of, for example, a gene product. Thus, specific functionalities such as antigenic domains can be screened with antibodies specific for those determinants.

In other embodiments of the invention, screening is preferably done with a cell-cell indicator assay. In this assay format, separate library cells (Cell A, the cell being assayed) and reporter cells (Cell B, the assay cell) are used. Only one component of the system, the library cells, is allowed to evolve. The screening is generally carried out in a two-dimensional immobilized format, such as on plates. The products of the metabolic pathways encoded by these genes (in this case, usually secondary metabolites such as antibiotics, polyketides, carotenoids, etc.) diffuse out of the library cell to the reporter cell. The product of the library cell may affect the reporter cell in one of a number of ways.

The assay system (indicator cell) can have a simple readout (e.g., green fluorescent protein, luciferase, β-galactosidase) which is induced by the library cell product but which does not affect the library cell. In these examples the desired product can be detected by calorimetric changes in the reporter cells adjacent to the library cell.

In other embodiments, indicator cells can in turn produce something that modifies the growth rate of the library cells via a feedback mechanism. Growth rate feedback can detect and accumulate very small differences. For example, if the library and reporter cells are competing for nutrients, library cells producing compounds to inhibit the growth of the reporter cells will have more available nutrients, and thus will have more opportunity for growth. This is a useful screen for antibiotics or a library of polyketide synthesis gene clusters where each of the library cells is expressing and exporting a different polyketide gene product.

Another variation of this theme is that the reporter cell for an antibiotic selection can itself secrete a toxin or antibiotic that inhibits growth of the library cell. Production by the library cell of an antibiotic that is able to suppress growth of the reporter cell will thus allow uninhibited growth of the library cell.

Conversely, if the library is being screened for production of a compound that stimulates the growth of the reporter cell (for example, in improving chemical syntheses, the library cell may supply nutrients such as amino acids to an auxotrophic reporter, or growth factors to a growth-factor-dependent reporter. The reporter cell in turn should produce a compound that stimulates the growth of the library cell. Interleukins, growth factors, and nutrients are possibilities.

Further possibilities include competition based on ability to kill surrounding cells, positive feedback loops in which the desired product made by the evolved cell stimulates the indicator cell to produce a positive growth factor for cell A, thus indirectly selecting for increased product formation.

In some embodiments of the invention it can be advantageous to use a different organism (or genetic background) for screening than the one that will be used in the final product. For example, markers can be added to DNA constructs used for recursive sequence recombination to make the microorganism dependent on the constructs during the improvement process, even though those markers may be undesirable in the final recombinant microorganism.

Likewise, in some embodiments it is advantageous to use a different substrate for screening an evolved enzyme than the one that will be used in the final product. For example, Evnin et al. (*Proc. Natl. Acad. Sci. U.S.A.* 87:6659–6663 (1990)) selected trypsin variants with altered substrate specificity by requiring that variant trypsin generate an essential amino acid for an arginine auxotroph by cleaving arginine β-naphthylamide. This is thus a selection for arginine-specific trypsin, with the growth rate of the host being proportional to that of the enzyme activity.

The pool of cells surviving screening and/or selection is enriched for recombinant genes conferring the desired phenotype (e.g. altered substrate specificity, altered biosynthetic ability, etc.). Further enrichment can be obtained, if desired, by performing a second round of screening and/or selection without generating additional diversity.

The recombinant gene or pool of such genes surviving one round of screening/selection forms one or more of the substrates for a second round of recombination. Again, recombination can be performed in vivo or in vitro by any of the recursive sequence recombination formats described above. If recursive sequence recombination is performed in vitro, the recombinant gene or genes to form the substrate for recombination should be extracted from the cells in which screening/selection was performed. Optionally, a subsequence of such gene or genes can be excised for more targeted subsequent recombination. If the recombinant gene(s) are contained within episomes, their isolation presents no difficulties. If the recombinant genes are chromosomally integrated, they can be isolated by amplification primed from known sequences flanking the regions in which recombination has occurred. Alternatively, whole genomic DNA can be isolated, optionally amplified, and used as the substrate for recombination. Small samples of genomic DNA can be amplified by whole genome amplification with degenerate primers (Barrett et al. *Nucleic Acids Research* 23:3488–3492 (1995)). These primers result in a large amount of random 3' ends, which can undergo homologous recombination when reintroduced into cells.

If the second round of recombination is to be performed in vivo, as is often the case, it can be performed in the cell surviving screening/selection, or the recombinant genes can be transferred to another cell type (e.g., a cell type having a high frequency of mutation and/or recombination). In this situation, recombination can be effected by introducing additional DNA segment(s) into cells bearing the recombinant genes. In other methods, the cells can be induced to exchange genetic information with each other by, for example, electroporation. In some methods, the second round of recombination is performed by dividing a pool of cells surviving screening/selection in the first round into two subpopulations. DNA from one subpopulation is isolated and transfected into the other population, where the recombinant gene(s) from the two subpopulations recombine to form a further library of recombinant genes. In these methods, it is not necessary to isolate particular genes from the first subpopulation or to take steps to avoid random shearing of DNA during extraction. Rather, the whole genome of DNA sheared or otherwise cleaved into manageable sized fragments is transfected into the second subpopulation. This approach is particularly useful when several genes are being evolved simultaneously and/or the location and identity of such genes within chromosome are not known.

The second round of recombination is sometimes performed exclusively among the recombinant molecules surviving selection. However, in other embodiments, additional substrates can be introduced. The additional substrates can be of the same form as the substrates used in the first round of recombination, i.e., additional natural or induced mutants of the gene or cluster of genes, forming the substrates for the first round. Alternatively, the additional substrate(s) in the second round of recombination can be exactly the same as the substrate(s) in the first round of replication.

After the second round of recombination, recombinant genes conferring the desired phenotype are again selected. The selection process proceeds essentially as before. If a suicide vector bearing a selective marker was used in the first round of selection, the same vector can be used again. Again, a cell or pool of cells surviving selection is selected. If a pool of cells, the cells can be subject to further enrichment.

III. Recursive Sequence Recombination of Genes For Bioremediation

Modern industry generates many pollutants for which the environment can no longer be considered an infinite sink. Naturally occurring microorganisms are able to metabolize thousands of organic compounds, including many not found in nature (e.g xenobiotics). Bioremediation, the deliberate use of microorganisms for the biodegradation of man-made wastes, is an emerging technology that offers cost and practicality advantages over traditional methods of disposal. The success of bioremediation depends on the availability of organisms that are able to detoxify or mineralize pollutants. Microorganisms capable of degrading specific pollutants can be generated by genetic engineering and recursive sequence recombination.

Although bioremediation is an aspect of pollution control, a more useful approach in the long term is one of prevention before industrial waste is pumped into the environment. Exposure of industrial waste streams to recursive sequence recombination-generated microorganisms capable of degrading the pollutants they contain would result in detoxification of mineralization of these pollutants before the waste stream enters the environment. Issues of releasing recombinant organisms can be avoided by containing them within bioreactors fitted to the industrial effluent pipes. This approach would also allow the microbial mixture used to be adjusted to best degrade the particular wastes being produced. Finally, this method would avoid the problems of adapting to the outside world and dealing with competition that face many laboratory microorganisms.

In the wild, microorganisms have evolved new catabolic activities enabling them to exploit pollutants as nutrient sources for which there is no competition. However, pollutants that are present at low concentrations in the environment may not provide a sufficient advantage to stimulate the evolution of catabolic enzymes. For a review of such naturally occurring evolution of biodegradative pathways and the manipulation of some of microorganisms by classical techniques, see Ramos et al., *Bio/Technology* 12:1349–1355 (1994).

Generation of new catabolic enzymes or pathways for bioremediation has thus relied upon deliberate transfer of specific genes between organisms (Wackett et al., supra), forced matings between bacteria with specific catabolic capabilities (Brenner et al. *Biodegradation* 5:359–377 (1994)), or prolonged selection in a chemostat. Some researchers have attempted to facilitate evolution via naturally occurring genetic mechanisms in their chemostat selections by including microorganisms with a variety of catabolic pathways (Kellogg et. al. *Science* 214:1133–1135 (1981); Chakrabarty *American Society of Micro. Biol. News* 62:130–137 (1996)). For a review of efforts in this area, see Cameron et al. *Applied Biochem. Biotech.* 38:105–140 (1993).

Current efforts in improving organisms for bioremediation take a labor-intensive approach in which many parameters are optimized independently, including transcription efficiency from native and heterologous promoters, regulatory circuits and translational efficiency as well as improvement of protein stability and activity (Timmis et al. *Ann. Rev. Microbiol.* 48:525–527 (1994)).

A recursive sequence recombination approach overcomes a number of limitations in the bioremediation capabilities of naturally occurring microorganisms. Both enzyme activity and specificity can be altered, simultaneously or sequentially, by the methods of the invention. For example, catabolic enzymes can be evolved to increase the rate at which they act on a substrate. Although knowledge of a rate-limiting step in a metabolic pathway is not required to practice the invention, rate-limiting proteins in pathways can be evolved to have increased expression and/or activity, the requirement for inducing substances can be eliminated, and enzymes can be evolved that catalyze novel reactions.

Some examples of chemical targets for bioremediation include but are not limited to benzene, xylene, and toluene, camphor, naphthalene, halogenated hydrocarbons, polychlorinated biphenyls (PCBs), trichlorethylene, pesticides such as pentachlorophenyls (PCPs), and herbicides such as atrazine.

A. Aromatic Hydrocarbons

Preferably, when an enzyme is "evolved" to have a new catalytic function, that function is expressed, either constitutively or in response to the new substrate. Recursive sequence recombination subjects both structural and regulatory elements (including the structure of regulatory proteins) of a protein to recombinogenic mutagenesis simultaneously. Selection of mutants that are efficiently able to use the new substrate as a nutrient source will be sufficient to ensure that both the enzyme and its regulation are optimized, without detailed analysis of either protein structure or operon regulation.

Examples of aromatic hydrocarbons include but are not limited to benzene, xylene, toluene, biphenyl, and polycyclic aromatic hydrocarbons such as pyrene and naphthalene. These compounds are metabolized via catechol intermediates. Degradation of catechol by *Pseudomonas putida* requires induction of the catabolic operon by cis, cis-muconate which acts on the CatR regulatory protein. The binding site for the CatR protein is G-$N_{11}$-A, while the optimal sequence for the LysR class of activators (of which CatR is a member) is T-$N_{11}$-A. Mutation of the G to a T in the CatR binding site enhances the expression of catechol metabolizing genes (Chakrabarty, *American Society of Microbiology News* 62:130–137 (1996)). This demonstrates that the control of existing catabolic pathways is not optimized for the metabolism of specific xenobiotics. It is also an example of a type of mutant that would be expected from recursive sequence recombination of the operon followed by selection of bacteria that are better able to degrade the target compound.

As an example of starting materials, dioxygenases are required for many pathways in which aromatic compounds are catabolized. Even small differences in dioxygenase sequence can lead to significant differences in substrate specificity (Furukawa et al. *J. Bact.* 175:5224–5232 (1993); Erickson et al. *App. Environ. Micro.* 59:3858–3862 (1993)). A hybrid enzyme made using sequences derived from two "parental" enzymes may possess catalytic activities that are intermediate between the parents (Erickson, ibid.), or may actually be better than either parent for a specific reaction (Furukawa et al. *J. Bact.* 176:2121–2123 (1994)). In one of these cases site directed mutagenesis was used to generate a single polypeptide with hybrid sequence (Erickson, ibid.); in the other, a four subunit enzyme was produced by expressing two subunits from each of two different dioxygenases (Furukawa, ibid.). Thus, sequences from one or more genes encoding dioxygenases can be used in the recursive sequence recombination techniques of the instant invention, to generate enzymes with new specificities. In addition, other features of the catabolic pathway can also be evolved using these techniques, simultaneously or sequentially, to optimize the metabolic pathway for an activity of interest.

B. Halogenated Hydrocarbons

Large quantities of halogenated hydrocarbons are produced annually for uses as solvents and biocides. These include, in the United States alone, over 5 million tons of both 1,2-dichloroethane and vinyl chloride used in PVC production in the U.S. alone. The compounds are largely not biodegradable by processes in single organisms, although in principle haloaromatic catabolic pathways can be constructed by combining genes from different microorganisms. Enzymes can be manipulated to change their substrate specificities. Recursive sequence recombination offers the possibility of tailoring enzyme specificity to new substrates without needing detailed structural analysis of the enzymes.

As an example of possible starting materials for the methods of the instant invention, Wackett et al. (*Nature* 368:627–629 (1994)) recently demonstrated that through classical techniques a recombinant Pseudomonas strain in which seven genes encoding two multi-component oxygenases are combined, generated a single host that can metabolize polyhalogenated compounds by sequential reductive and oxidative techniques to yield non-toxic products. These and/or related materials can be subjected to the techniques discussed above so as to evolve and optimize a biodegradative pathway in a single organism.

Trichloroethylene is a significant groundwater contaminant. It is degraded by microorganisms in a cometabolic way (i.e., no energy or nutrients are derived). The enzyme must be induced by a different compound (e.g., *Pseudomonas cepacia* uses toluene-4-monoxygenase, which requires induction by toluene, to destroy trichloroethylene). Furthermore, the degradation pathway involves formation of highly reactive epoxides that can inactivate the enzyme (Timmis et al. *Ann. Rev. Microbiol.* 48:525–557 (1994)). The recursive sequence recombination techniques of the invention could be used to mutate the enzyme and its regulatory region such that it is produced constitutively, and is less susceptible to epoxide inactivation. In some embodiments of the invention, selection of hosts constitutively producing the enzyme and less susceptible to the epoxides can be accomplished by demanding growth in the presence of increasing concentrations of trichloroethylene in the absence of inducing substances.

C. Polychlorinated Biphenyls (PCBs) and Polycyclic Aromatic Hydrocarbons (PAHs)

PCBs and PAHs are families of structurally related compounds that are major pollutants at many Superfund sites. Bacteria transformed with plasmids encoding enzymes with broader substrate specificity have been used commercially. In nature, no known pathways have been generated in a single host that degrade the larger PAHs or more heavily chlorinated PCBs. Indeed, often the collaboration of anaerobic and aerobic bacteria are required for complete metabolism.

Thus, likely sources for starting material for recursive sequence recombination include identified genes encoding PAH-degrading catabolic pathways on large (20–100 KB) plasmids (Sanseverino et al. *Applied Environ. Micro.* 59:1931–1937 (1993); Simon et al. *Gene* 127:31–37 (1993); Zylstra et al. *Annals of the NY Acad. Sci.* 721:386–398 (1994)); while biphenyl and PCB-metabolizing enzymes are encoded by chromosomal gene clusters, and in a number of cases have been cloned onto plasmids (Hayase et al. *J. Bacteriol.* 172:1160–1164 (1990); Furukawa et al. *Gene* 98:21–28 (1992); Hofer et al. *Gene* 144:9–16 (1994)). The materials can be subjected to the techniques discussed above so as to evolve a biodegradative pathway in a single organism.

Substrate specificity in the PCB pathway largely results from enzymes involved in initial dioxygenation reactions, and can be significantly altered by mutations in those enzymes (Erickson et al. *Applied Environ. Micro.* 59:3858–38662 (1993); Furukawa et al. *J. Bact.* 175:5224–5232 (1993). Mineralization of PAHs and PCBs requires that the downstream pathway is able to metabolize the products of the initial reaction (Brenner et al. *Biodegradation* 5:359–377 (1994)). In this case, recursive sequence recombination of the entire pathway with selection for bacteria able to use the PCB or PAH as the sole carbon source will allow production of novel PCB and PAH degrading bacteria.

D. Herbicides

A general method for evolving genes for the catabolism of insoluble herbicides is exemplified as follows for atrazine. Atrazine [2-chloro-4-(ethylamino)-6-(isopropylamino)-1,3, 5-triazine] is a moderately persistent herbicide which is frequently detected in ground and surface water at concentrations exceeding the 3 ppb health advisory level set by the EPA. Atrazine can be slowly metabolized by a Pseudomonas species (Mandelbaum et al. *Appl. Environ.Micro.* 61:1451–1457 (1995)). The enzymes catalyzing the first two steps in atrazine metabolism by Pseudomonas are encoded by genes AtzA and AtzB (de Souza et al. *Appl. Environ. Micro.* 61:3373–3378 (1995)). These genes have been cloned in a 6.8 kb fragment into pUC18 (AtzAB-pUC). *E. coli* carrying this plasmid converts atrazine to much more soluble metabolites. It is thus possible to screen for enzyme activity by growing bacteria on plates containing atrazine. The herbicide forms an opaque precipitate in the plates, but cells containing AtzAB-pU18 secrete atrazine degrading enzymes, leading to a clear halo around those cells or colonies. Typically, the size of the halo and the rate of its formation can be used to assess the level of activity so that picking colonies with the largest halos allows selection of the more active or highly produced atrazine degrading enzymes. Thus, the plasmids carrying these genes can be subjected to the recursive sequence recombination formats described above to optimize the catabolism of atrazine in *E. coli* or another host of choice, including Pseudomonas. After each round of recombination, screening of host colonies expressing the evolved genes can be done on agar plates containing atrazine to observe halo formation. This is a generally applicable method for screening enzymes that metabolize insoluble compounds to those that are soluble (e.g., polycyclicaromatic hydrocarbons). Additionally, catabolism of atrazine can provide a source of nitrogen for the cell; if no other nitrogen is available, cell growth will be limited by the rate at which the cells can catabolize nitrogen. Cells able to utilize atrazine as a nitrogen source can thus be selected from a background of non-utilizers or poor-utilizers.

E. Heavy Metal Detoxification

Bacteria are used commercially to detoxify arsenate waste generated by the mining of arsenopyrite gold ores. As well as mining effluent, industrial waste water is often contaminated with heavy metals (e.g., those used in the manufacture of electronic components and plastics). Thus, simply to be able to perform other bioremedial functions, microorganisms must be resistant to the levels of heavy metals present, including mercury, arsenate, chromate, cadmium, silver, etc.

A strong selective pressure is the ability to metabolize a toxic compound to one less toxic. Heavy metals are toxic largely by virtue of their ability to denature proteins (Ford et al. *Bioextraction and Biodeterioration of Metals*, p. 1–23). Detoxification of heavy metal contamination can be effected in a number of ways including changing the solubility or bioavailability of the metal, changing its redox state (e.g. toxic mercuric chloride is detoxified by reduction to the much more volatile elemental mercury) and even by bioaccumulation of the metal by immobilized bacteria or plants. The accumulation of metals to a sufficiently high concentration allows metal to be recycled; smelting burns off the organic part of the organism, leaving behind reusable accumulated metal. Resistances to a number of heavy metals (arsenate, cadmium, cobalt, chromium, copper, mercury, nickel, lead, silver, and zinc) are plasmid encoded in a number of species including Staphylococcus and Pseudomonas (Silver et al. *Environ. Health Perspect.* 102:107–113 (1994); Ji et al. *J. Ind. Micro.* 14:61–75 (1995)). These genes also confer heavy metal resistance on other species as well (e.g., *E. coli*). The recursive sequence recombination techniques of the instant invention (RSR) can be used to increase microbial heavy metal tolerances, as well as to increase the extent to which cells will accumulate heavy metals. For example, the ability of *E. coli* to detoxify arsenate can be improved at least 100-fold by RSR (see co-pending application Ser. No. 08/621,859, filed Mar. 25, 1996).

Cyanide is very efficiently used to extract gold from rock containing as little as 0.2 oz per ton. This cyanide can be microbially neutralized and used as a nitrogen source by fungi or bacteria such as *Pseudomonas fluorescens*. A problem with microbial cyanide degradation is the presence of toxic heavy metals in the leachate. RSR can be used to increase the resistance of bioremedial microorganisms to toxic heavy metals, so that they will be able to survive the levels present in many industrial and Superfund sites. This will allow them to biodegrade organic pollutants including but not limited to aromatic hydrocarbons, halogenated hydrocarbons, and biocides.

F. Microbial Mining

"Bioleaching" is the process by which microbes convert insoluble metal deposits (usually metal sulfides or oxides) into soluble metal sulfates. Bioleaching is commercially important in the mining of arsenopyrite, but has additional potential in the detoxification and recovery of metals and acids from waste dumps. Naturally occurring bacteria capable of bioleaching are reviewed by Rawlings and Silver (*Bio/Technology* 13:773–778 (1995)). These bacteria are typically divided into groups by their preferred temperatures for growth. The more important mesophiles are Thiobacillus and Leptospirillum species. Moderate thermophiles include Sulfobacillus species. Extreme thermophiles include Sulfolobus species. Many of these organisms are difficult to grow in commercial industrial settings, making their catabolic abilities attractive candidates for transfer to and optimization in other organisms such as Pseudomonas, Rhodococcus, *T. ferrooxidans* or *E. coli*. Genetic systems are available for at least one strain of *T. ferrooxidans*, allowing the manipulation of its genetic material on plasmids.

The recursive sequence recombination methods described above can be used to optimize the catalytic abilities in native hosts or heterologous hosts for evolved bioleaching genes or pathways, such as the ability to convert metals from insoluble to soluble salts. In addition, leach rates of particular ores can be improved as a result of, for example, increased resistance to toxic compounds in the ore concentrate, increased specificity for certain substrates, ability to use different substrates as nutrient sources, and so on.

G. Oil Desulfurization

The presence of sulfur in fossil fuels has been correlated with corrosion of pipelines, pumping, and refining equipment, and with the premature breakdown of combustion engines. Sulfur also poisons many catalysts used in the refining of fossil fuels. The atmospheric emission of sulfur combustion products is known as acid rain.

Microbial desulfurization is an appealing bioremediation application. Several bacteria have been reported that are capable of catabolizing dibenzothiophene (DBT), which is the representative compound of the class of sulfur compounds found in fossil fuels. U.S. Pat. No. 5,356,801 discloses the cloning of a DNA molecule from *Rhodococcus rhodochrous* capable of biocatalyzing the desulfurization of oil. Denome et al. (*Gene* 175:6890–6901 (1995)) disclose the cloning of a 9.8 kb DNA fragment from Pseudomonas encoding the upper naphthalene catabolizing pathway which also degrades dibenzothiophene. Other genes have been identified that perform similar functions (disclosed in U.S. Pat. No. 5,356,801).

The activity of these enzymes is currently too low to be commercially viable, but the pathway could be increased in efficiency using the recursive sequence recombination techniques of the invention. The desired property of the genes of interest is their ability to desulfurize dibenzothiophene. In some embodiments of the invention, selection is preferably accomplished by coupling this pathway to one providing a nutrient to the bacteria. Thus, for example, desulfurization of dibenzothiophene results in formation of hydroxybiphenyl. This is a substrate for the biphenyl-catabolizing pathway which provides carbon and energy. Selection would thus be done by "shuffling" the dibenzothiophene genes and transforming them into a host containing the biphenyl-catabolizing pathway. Increased dibenzothiophene desulfurization will result in increased nutrient availability and increased growth rate. Once the genes have been evolved they are easily separated from the biphenyl degrading genes. The latter are undesirable in the final product since the object is to desulfurize without decreasing the energy content of the oil.

H. Organo-Nitro Compounds

Organo-nitro compounds are used as explosives, dyes, drugs, polymers and antimicrobial agents. Biodegradation of these compounds occurs usually by way of reduction of the nitrate group, catalyzed by nitroreductases, a family of broadly-specific enzymes. Partial reduction of organo-nitro compounds often results in the formation of a compound more toxic than the original (Hassan et al. 1979 *Arch Bioch Biop.* 196:385–395). Recursive sequence recombination of nitroreductases can produce enzymes that are more specific, and able to more completely reduce (and thus detoxify) their target compounds (examples of which include but are not limited to nitrotoluenes and nitrobenzenes). Nitroreductases can be isolated from bacteria isolated from explosive-contaminated soils, such as *Morganella morganii* and *Enterobacter cloacae* (Bryant et. al., 1991. *J. Biol Chem.* 266:4126–4130). A preferred selection method is to look for increased resistance to the organo-nitro compound of interest, since that will indicate that the enzyme is also able to reduce any toxic partial reduction products of the original compound.

IV. Use of Alternative Substrates for Chemical Synthesis

Metabolic engineering can be used to alter microorganisms that produce industrially useful chemicals, so that they will grow using alternate and more abundant sources of nutrients, including human-produced industrial wastes. This typically involves providing both a transport system to get the alternative substrate into the engineered cells and catabolic enzymes from the natural host organisms to the engineered cells. In some instances, enzymes can be secreted into the medium by engineered cells to degrade the alternate substrate into a form that can more readily be taken up by the engineered cells; in other instances, a batch of engineered cells can be grown on one preferred substrate, then lysed to liberate hydrolytic enzymes for the alternate substrate into the medium, while a second inoculum of the same engineered host or a second host is added to utilize the hydrolyzate.

The starting materials for recursive sequence recombination will typically be genes for utilization of a substrate or its transport. Examples of nutrient sources of interest include but are not limited to lactose, whey, galactose, mannitol, xylan, cellobiose, cellulose and sucrose, thus allowing cheaper production of compounds including but not limited to ethanol, tryptophan, rhamnolipid surfactants, xanthan gum, and polyhydroxylalkanoate. For a review of such substrates as desired target substances, see Cameron et al. (*Appl. Biochem. Biotechnol.* 38:105–140 (1993)).

The recursive sequence recombination methods described above can be used to optimize the ability of native hosts or heterologous hosts to utilize a substrate of interest, to evolve more efficient transport systems, to increase or alter specificity for certain substrates, and so on.

V. Biosynthesis

Metabolic engineering can be used to alter organisms to optimize the production of practically any metabolic intermediate, including antibiotics, vitamins, amino acids such as phenylalanine and aromatic amino acids, ethanol, butanol, polymers such as xanthan gum and bacterial cellulose, peptides, and lipids. When such compounds are already produced by a host, the recursive sequence recombination techniques described above can be used to optimize production of the desired metabolic intermediate, including such features as increasing enzyme substrate specificity and turnover number, altering metabolic fluxes to reduce the concentrations of toxic substrates or intermediates, increasing resistance of the host to such toxic compounds, eliminating, reducing or altering the need for inducers of gene expression/activity, increasing the production of enzymes necessary for metabolism, etc.

Enzymes can also be evolved for improved activity in solvents other than water. This is useful because intermediates in chemical syntheses are often protected by blocking groups which dramatically affect the solubility of the compound in aqueous solvents. Many compounds can be produced by a combination of pure chemical and enzymically catalyzed reactions. Performing enzymic reactions on almost insoluble substrates is clearly very inefficient, so the availability of enzymes that are active in other solvents will be of great use. One example of such a scheme is the evolution of a paranitrobenzyl esterase to remove protecting groups from an intermediate in loracarbef synthesis (Moore, J. C. and Arnold, F. H. *Nature Biotechnology* 14:458–467 (1996)). In this case alternating rounds of error-prone PCR and colony screening for production of a fluorescent reporter from a substrate analogue were used to generate a mutant esterase that was 16-fold more active than the parent molecule in 30% dimethylformamide. No individual mutation was found to contribute more than a 2-fold increase in activity, but it was the combination of a number of mutations which led to the overall increase. Structural analysis of the mutant protein showed that the amino acid changes were distributed throughout the length of the protein in a manner that could not have been rationally predicted. Sequential rounds of error-prone PCR have the problem that after each round all but one mutant is discarded, with a concomitant loss of information contained in all the other beneficial mutations. Recursive sequence recombination avoids this problem, and would thus be ideally suited to evolving enzymes for catalysis in other solvents, as well as in conditions where salt concentrations or pH were different from the original enzyme optimas.

In addition, the yield of almost any metabolic pathway can be increased, whether consisting entirely of genes endogenous to the host organisms or all or partly heterologous genes. Optimization of the expression levels of the enzymes in a pathway is more complex than simply maximizing expression. In some cases regulation, rather than constitutive expression of an enzyme may be advantageous for cell growth and therefore for product yield, as seen for production of phenylalanine (Backman et al. *Ann. NY Acad. Sci.* 589:16–24 (1990)) and 2-keto-L-gluconic acid (Anderson et al. U.S. Pat. No. 5,032,514). In addition, it is often advantageous for industrial purposes to express proteins in organisms other than their original hosts. New host strains may be preferable for a variety of reasons, including ease of cloning and transformation, pathogenicity, ability to survive in particular environments and a knowledge of the physiology and genetics of the organisms. However, proteins expressed in heterologous organisms often show markedly reduced activity for a variety of reasons including inability to fold properly in the new host (Sarthy et al. *Appl. Environ. Micro.* 53:1996–2000 (1987)). Such difficulties can indeed be overcome by the recursive sequence recombination strategies of the instant invention.

A. Antibiotics

The range of natural small molecule antibiotics includes but is not limited to peptides, peptidolactones, thiopeptides, beta-lactams, glycopeptides, lantibiotics, microcins, polyketide-derived antibiotics (anthracyclins, tetracyclins, macrolides, avermectins, polyethers and ansamycins), chloramphenicol, aminoglycosides, aminocyclitols, polyoxins, agrocins and isoprenoids.

There are at least three ways in which recursive sequence recombination techniques of the instant invention can be used to facilitate novel drug synthesis, or to improve biosynthesis of existing antibiotics.

First, antibiotic synthesis enzymes can be "evolved" together with transport systems that allow entry of compounds used as antibiotic precursors to improve uptake and incorporation of function-altering artificial side chain precursors. For example, penicillin V is produced by feeding Penicillium the artificial side chain precursor phenoxyacetic acid, and LY146032 by feeding *Streptomyces roseosporus* decanoic acid (Hopwood, *Phil. Trans. R. Soc. Lond.* B 324:549–562 (1989)). Poor precursor uptake and poor incorporation by the synthesizing enzyme often lead to inefficient formation of the desired product. Recursive sequence recombination of these two systems can increase the yield of desired product.

Furthermore, a combinatorial approach can be taken in which an enzyme is shuffled for novel catalytic activity/substrate recognition (perhaps by including randomizing oligonucleotides in key positions such as the active site). A number of different substrates (for example, analogues of side chains that are normally incorporated into the antibiotic) can then be tested in combination with all the different enzymes and tested for biological activity. In this embodiment, plates are made containing different potential antibiotic precursors (such as the side chain analogues). The microorganisms containing the shuffled library (the library strain) are replicated onto those plates, together with a competing, antibiotic sensitive, microorganism (the indicator strain). Library cells that are able to incorporate the new side chain to produce an effective antibiotic will thus be able to compete with the indicator strain, and will be selected for.

Second, the expression of heterologous genes transferred from one antibiotic synthesizing organism to another can be optimized. The newly introduced enzyme(s) act on secondary metabolites in the host cell, transforming them into new compounds with novel properties. Using traditional methods, introduction of foreign genes into antibiotic synthesizing hosts has already resulted in the production of novel hybrid antibiotics. Examples include mederrhodin, dihydrogranatirhodin, 6-deoxyerythromycin A, isovalerylspiramycin and other hybrid macrolides (Cameron et. al. *Appl. Biochem. Biotechnol.* 38:105–140 (1993)). The recursive sequence recombination techniques of the instant invention can be used to optimize expression of the foreign genes, to stabilize the enzyme in the new host cell, and to increase the activity of the introduced enzyme against its new substrates in the new host cell. In some embodiments of the invention, the host genome may also be so optimized.

Third, the substrate specificity of an enzyme involved in secondary metabolism can be altered so that it will act on and modify a new compound or so that its activity is changed and it acts at a different subset of positions of its normal substrate. Recursive sequence recombination can be used to alter the substrate specificities of enzymes. Furthermore, in addition to recursive sequence recombination of individual enzymes being a strategy to generate novel antibiotics, recursive sequence recombination of entire pathways, by altering enzyme ratios, will alter metabolite fluxes and may result, not only in increased antibiotic synthesis, but also in the synthesis of different antibiotics. This can be deduced from the observation that expression of different genes from the same cluster in a foreign host leads to different products being formed (see p. 80 in Hutchinson et. al., (1991) *Ann NY Acad Sci,* 646:78–93). Recursive sequence recombination of the introduced gene clusters may result in a variety of expression levels of different proteins within the cluster (because it produces different combinations of, in this case regulatory, mutations). This in turn may lead to a variety of different end products. Thus, "evolution"

of an existing antibiotic synthesizing pathway could be used to generate novel antibiotics either by modifying the rates or substrate specificities of enzymes in that pathway.

Additionally, antibiotics can also be produced in vitro by the action of a purified enzyme on a precursor. For example isopenicillin N synthase catalyses the cyclization of many analogues of its normal substrate (d-(L-a-aminoadipyl)-L-cysteinyl-D-valine) (Hutchinson, Med. Res. Rev. 8:557–567 (1988)). Many of these products are active as antibiotics. A wide variety of substrate analogues can be tested for incorporation by secondary metabolite synthesizing enzymes without concern for the initial efficiency of the reaction. Recursive sequence recombination can be used subsequently to increase the rate of reaction with a promising new substrate.

Thus, organisms already producing a desired antibiotic can be evolved with the recursive sequence recombination techniques described above to maximize production of that antibiotic. Additionally, new antibiotics can be evolved by manipulation of genetic material from the host by the recursive sequence recombination techniques described above. Genes for antibiotic production can be transferred to a preferred host after cycles of recursive sequence recombination or can be evolved in the preferred host as described above. Antibiotic genes are generally clustered and are often positively regulated, making them especially attractive candidates for the recursive sequence recombination techniques of the instant invention. Additionally, some genes of related pathways show cross-hybridization, making them preferred candidates for the generation of new pathways for new antibiotics by the recursive sequence recombination techniques of the invention. Furthermore, increases in secondary metabolite production including enhancement of substrate fluxes (by increasing the rate of a rate limiting enzyme, deregulation of the pathway by suppression of negative control elements or over expression of activators and the relief of feedback controls by mutation of the regulated enzyme to a feedback-insensitive deregulated protein) can be achieved by recursive sequence recombination without exhaustive analysis of the regulatory mechanisms governing expression of the relevant gene clusters.

The host chosen for expression of evolved genes is preferably resistant to the antibiotic produced, although in some instances production methods can be designed so as to sacrifice host cells when the amount of antibiotic produced is commercially significant yet lethal to the host. Similarly, bioreactors can be designed so that the growth medium is continually replenished, thereby "drawing off" antibiotic produced and sparing the lives of the producing cells. Preferably, the mechanism of resistance is not the degradation of the antibiotic produced.

Numerous screening methods for increased antibiotic expression are known in the art, as discussed above, including screening for organisms that are more resistant to the antibiotic that they produce. This may result from linkage between expression of the antibiotic synthesis and antibiotic resistance genes (Chater, Bio/Technology 8:115–121 (1990)). Another screening method is to fuse a reporter gene (e.g. xylE from the Pseudomonas TOL plasmid) to the antibiotic production genes. Antibiotic synthesis gene expression can then be measured by looking for expression of the reporter (e.g. xylE encodes a catechol dioxygenase which produces yellow muconic semialdehyde when colonies are sprayed with catechol (Zukowski et al. Proc. Natl. Acad. Sci. U.S.A. 80:1101–1105 (1983)).

The wide variety of cloned antibiotic genes provides a wealth of starting materials for the recursive sequence recombination techniques of the instant invention. For example, genes have been cloned from Streptomyces cattleya which direct cephamycin C synthesis in the non-antibiotic producer Streptomyces lividans (Chen et al. Bio/Technology 6:1222–1224 (1988)). Clustered genes for penicillin biosynthesis (δ-(L-α-aminoadipyl)-L-cysteinyl-D-valine synthetase; isopenicillin N synthetase and acyl coenzyme A:6-aminopenicillanic acid acyltransferase) have been cloned from Penicillium chrysogenum. Transfer of these genes into Neurospora crassa and Aspergillus niger result in the synthesis of active penicillin V (Smith et al. Bio/Technology 8:39–41 (1990)). For a review of cloned genes involved in Cephalosporin C, Penicillins G and V and Cephamycin C biosynthesis, see Piepersberg, Crit. Rev. Biotechnol. 14:251–285 (1994). For a review of cloned clusters of antibiotic-producing genes, see Chater Bio/Technology 8:115–121 (1990). Other examples of antibiotic synthesis genes transferred to industrial producing strains, or over expression of genes, include tylosin, cephamycin C, cephalosporin C, LL-E33288 complex (an antitumor and antibacterial agent), doxorubicin, spiramycin and other macrolide antibiotics, reviewed in Cameron et al. Appl. Biochem. Biotechnol. 38:105–140 (1993).

B. Biosynthesis to Replace Chemical Synthesis of Antibiotics

Some antibiotics are currently made by chemical modifications of biologically produced starting compounds. Complete biosynthesis of the desired molecules may currently be impractical because of the lack of an enzyme with the required enzymatic activity and substrate specificity. For example, 7-aminodeacetooxycephalosporanic acid (7-ADCA) is a precursor for semi-synthetically produced cephalosporins. 7-ADCA is made by a chemical ring expansion from penicillin V followed by enzymatic deacylation of the phenoxyacetal group. Cephalosporin V could in principle be produced biologically from penicillin V using penicillin N expandase, but penicillin V is not used as a substrate by any known expandase. The recursive sequence recombination techniques of the invention can be used to alter the enzyme so that it will use penicillin V as a substrate. Similarly, penicillin transacylase could be so modified to accept cephalosporins or cephamycins as substrates.

In yet another example, penicillin amidase expressed in E. coli is a key enzyme in the production of penicillin G derivatives. The enzyme is generated from a precursor peptide and tends to accumulate as insoluble aggregates in the periplasm unless non-metabolizable sugars are present in the medium (Scherrer et al. Appl. Microbiol. Biotechnol. 42:85–91 (1994)). Evolution of this enzyme through the methods of the instant invention could be used to generate an enzyme that folds better, leading to a higher level of active enzyme expression.

In yet another example, Penicillin G acylase covalently linked to agarose is used in the synthesis of penicillin G derivatives. The enzyme can be stabilized for increased activity, longevity and/or thermal stability by chemical modification (Fernandez-Lafuente et. al. Enzyme Microb. Technol. 14:489–495 (1992). Increased thermal stability is an especially attractive application of the recursive sequence recombination techniques of the instant invention, which can obviate the need for the chemical modification of such enzymes. Selection for thermostability can be performed in vivo in E. coli or in thermophiles at higher temperatures. In general, thermostability is a good first step in enhancing general stabilization of enzymes. Random mutagenesis and selection can also be used to adapt enzymes to function in non-aqueous solvents (Arnold Curr Opin Biotechnol, 4:450–455 (1993); Chen et. al. *Proc. Natl. Acad. Sci. U.S.A.*, 90:5618–5622 (1993)). Recursive sequence recombination represents a more powerful (since recombinogenic) method of generating mutant enzymes that are stable and active in non-aqueous environments. Additional screening can be done on the basis of enzyme stability in solvents.

C. Polyketides

Polyketides include antibiotics such as tetracycline and erythromycin, anti-cancer agents such as daunomycin, immunosuppressants such as FK506 and rapamycin and veterinary products such as monesin and avermectin. Polyketide synthases (PKS's) are multifunctional enzymes that control the chain length, choice of chain-building units and reductive cycle that generates the huge variation in naturally occurring polyketides. Polyketides are built up by sequential transfers of "extender units" (fatty acyl CoA groups) onto the appropriate starter unit (examples are acetate, coumarate, propionate and malonamide). The PKS's determine the number of condensation reactions and the type of extender groups added and may also fold and cyclize the polyketide precursor. PKS's reduce specific β-keto groups and may dehydrate the resultant β-hydroxyls to form double bonds. Modifications of the nature or number of building blocks used, positions at which β-keto groups are reduced, the extent of reduction and different positions of possible cyclizations, result in formation of different final products. Polyketide research is currently focused on modification and inhibitor studies, site directed mutagenesis and 3-D structure elucidation to lay the groundwork for rational changes in enzymes that will lead to new polyketide products.

Recently, McDaniel et al. (*Science* 262:1546–1550 (1995)) have developed a Streptomyces host-vector system for efficient construction and expression of recombinant PKSs. Hutchinson (*Bio/Technology* 12:375–308 (1994)) reviewed targeted mutation of specific biosynthetic genes and suggested that microbial isolates can be screened by DNA hybridization for genes associated with known pharmacologically active agents so as to provide new metabolites and large amounts of old ones. In particular, that review focuses on polyketide synthase and pathways to aminoglycoside and oligopeptide antibiotics.

The recursive sequence recombination techniques of the instant invention can be used to generate modified enzymes that produce novel polyketides without such detailed analytical effort. The availability of the PKS genes on plasmids and the existence of *E. coli*-Streptomyces shuttle vectors (Wehmeier *Gene* 165:149–150 (1995)) makes the process of recursive sequence recombination especially attractive by the techniques described above. Techniques for selection of antibiotic producing organisms can be used as described above; additionally, in some embodiments screening for a particular desired polyketide activity or compound is preferable.

D. Isoprenoids

Isoprenoids result from cyclization of farnesyl pyrophosphate by sesquiterpene synthases. The diversity of isoprenoids is generated not by the backbone, but by control of cyclization. Cloned examples of isoprenoid synthesis genes include trichodiene synthase from *Fusarium sprorotrichioides*, pentalene synthase from Streptomyces, aristolochene synthase from *Penicillium roquefortii*, and epi-aristolochene synthase from *N. tabacum* (Cane, D. E. (1995). Isoprenoid antibiotics, pages 633–655, in "Genetics and Biochemistry of Antibiotic Production" edited by Vining, L. C. & Stuttard, C., published by Butterworth-Heinemann). Recursive sequence recombination of sesquiterpene synthases will be of use both in allowing expression of these enzymes in heterologous hosts (such as plants and industrial microbial strains) and in alteration of enzymes to change the cyclized product made. A large number of isoprenoids are active as antiviral, antibacterial, antifungal, herbicidal, insecticidal or cytostatic agents. Antibacterial and antifungal isoprenoids could thus be preferably screened for using the indicator cell type system described above, with the producing cell competing with bacteria or fungi for nutrients. Antiviral isoprenoids could be screened for preferably by their ability to confer resistance to viral attack on the producing cell.

E. Bioactive Peptide Derivatives

Examples of bioactive non-ribosomally synthesized peptides include the antibiotics cyclosporin, pepstatin, actinomycin, gramicidin, depsipeptides, vancomycin, etc. These peptide derivatives are synthesized by complex enzymes rather than ribosomes. Again, increasing the yield of such non-ribosomally synthesized peptide antibiotics has thus far been done by genetic identification of biosynthetic "bottlenecks" and over expression of specific enzymes (See, for example, p. 133–135 in "Genetics and Biochemistry of Antibiotic Production" edited by Vining, L. C. & Stuttard, C., published by Butterworth-Heinemann). Recursive sequence recombination of the enzyme clusters can be used to improve the yields of existing bioactive non-ribosomally made peptides in both natural and heterologous hosts. Like polyketide synthases, peptide synthases are modular and multifunctional enzymes catalyzing condensation reactions between activated building blocks (in this case amino acids) followed by modifications of those building blocks (see Kleinkauf, H. and von Dohren, H. *Eur. J. Biochem.* 236:335–351 (1996)). Thus, as for polyketide synthases, recursive sequence recombination can also be used to alter peptide synthases: modifying the specificity of the amino acid recognized by each binding site on the enzyme and altering the activity or substrate specificities of sites that modify these amino acids to produce novel compounds with antibiotic activity.

Other peptide antibiotics are made ribosomally and then post-translationally modified. Examples of this type of antibiotics are lantibiotics (produced by gram positive bacteria such Staphylococcus, Streptomyces, Bacillus, and Actinoplanes) and microcins (produced by Enterobacteriaceae). Modifications of the original peptide include (in lantibiotics) dehydration of serine and threonine, condensation of dehydroamino acids with cysteine, or simple N- and C-terminal blocking (microcins). For ribosomally made antibiotics both the peptide-encoding sequence and the modifying enzymes may have their expression levels modified by recursive sequence recombination. Again, this will lead to both increased levels of antibiotic synthesis, and by modulation of the levels of the modifying enzymes (and the sequence of the ribosomally synthesized peptide itself) novel antibiotics.

Screening can be done as for other antibiotics as described above, including competition with a sensitive (or even initially insensitive) microbial species. Use of competing bacteria that have resistances to the antibiotic being produced will select strongly either for greatly elevated levels of that antibiotic (so that it swamps out the resistance mechanism) or for novel derivatives of that antibiotic that are not neutralized by the resistance mechanism.

F. Polymers

Several examples of metabolic engineering to produce biopolymers have been reported, including the production of the biodegradable plastic polyhydroxybutarate (PHB), and the polysaccharide xanthan gum. For a review, see Cameron et al. *Applied Biochem. Biotech.* 38:105–140 (1993). Genes for these pathways have been cloned, making them excellent candidates for the recursive sequence recombination techniques described above. Expression of such evolved genes in a commercially viable host such as *E. coli* is an especially attractive application of this technology.

Examples of starting materials for recursive sequence recombination include but are not limited to genes from bacteria such as Alcaligenes, Zoogloea, Rhizobium, Bacillus, and Azobacter, which produce polyhydroxyalkanoates (PHAs) such as polyhyroxybutyrate (PHB) intracellularly as energy reserve materials in response to stress. Genes from *Alcaligenes eutrophus* that encode enzymes catalyzing the conversion of acetoacetyl CoA to PHB have been transferred both to *E. coli* and to the plant *Arabidopsis thaliana* (Poirier et al. *Science* 256:520–523 (1992)). Two of these genes (phbB and phbC, encoding acetoacetyl-CoA reductase and PHB synthase respectively) allow production of PHB in Arabidopsis. The plants producing the plastic are stunted, probably because of adverse interactions between the new metabolic pathway and the plants' original metabolism (i.e., depletion of substrate from the mevalonate pathway). Improved production of PHB in plants has been attempted by localization of the pathway enzymes to organelles such as plastids. Other strategies such as regulation of tissue specificity, expression timing and cellular localization have been suggested to solve the deleterious effects of PHB expression in plants. The recursive sequence recombination techniques of the invention can be used to modify such heterologous genes as well as specific cloned interacting pathways (e.g., mevalonate), and to optimize PHB synthesis in industrial microbial strains, for example to remove the requirement for stresses (such as nitrogen limitation) in growth conditions.

Additionally, other microbial polyesters are made by different bacteria in which additional monomers are incorporated into the polymer (Peoples et al. in Novel Biodegradable Microbial Polymers, EA Dawes, ed., pp191–202 (1990)). Recursive sequence recombination of these genes or pathways singly or in combination into a heterologous host will allow the production of a variety of polymers with differing properties, including variation of the monomer subunit ratios in the polymer. Another polymer whose synthesis may be manipulated by recursive sequence recombination is cellulose. The genes for cellulose biosynthesis have been cloned from *Agrobacterium tumefaciens* (Matthysse, A. G. et. al. *J. Bacteriol.* 177:1069–1075 (1995)). Recursive sequence recombination of this biosynthetic pathway could be used either to increase synthesis of cellulose, or to produce mutants in which alternative sugars are incorporated into the polymer.

G. Carotenoids

Carotenoids are a family of over 600 terpenoids produced in the general isoprenoid biosynthetic pathway by bacteria, fungi and plants (for a review, see Armstrong, *J. Bact.* 176:4795–4802 (1994)). These pigments protect organisms against photooxidative damage as well as functioning as anti-tumor agents, free radical-scavenging anti-oxidants, and enhancers of the immune response. Additionally, they are used commercially in pigmentation of cultured fish and shellfish. Examples of carotenoids include but are not limited to myxobacton, spheroidene, spheroidenone, lutein, astaxanthin, violaxanthin, 4-ketorulene, myxoxanthrophyll, echinenone, lycopene, zeaxanthin and its mono- and diglucosides, $\alpha$-, $\beta$-, $\gamma$- and $\delta$-carotene, $\beta$-cryptoxanthin monoglucoside and neoxanthin.

Carotenoid synthesis is catalyzed by relatively small numbers of clustered genes: 11 different genes within 12 kb of DNA from *Myxococcus xanthus* (Botella et al. *Eur. J. Biochem.* 233:238–248 (1995)) and 8 genes within 9 kb of DNA from *Rhodobacter sphaeroides* (Lang et. al. *J. Bact.* 177:2064–2073 (1995)). In some microorganisms, such as *Thermus thermophilus*, these genes are plasmid-borne (Tabata et al. *FEBS Letts* 341:251–255 (1994)). These features make carotenoid synthetic pathways especially attractive candidates for recursive sequence recombination.

Transfer of some carotenoid genes into heterologous organisms results in expression. For example, genes from *Erwina uredovora* and *Haematococcus pluvialis* will function together in *E. coli* (Kajiwara et al. *Plant Mol. Biol.* 29:343–352 (1995)). *E. herbicola* genes will function in *R. sphaeroides* (Hunter et al. *J. Bact.* 176:3692–3697 (1994)). However, some other genes do not; for example, *R. capsulatus* genes do not direct carotenoid synthesis in *E. coli* (Marrs, *J. Bact.* 146:1003–1012 (1981)).

In an embodiment of the invention, the recursive sequence recombination techniques of the invention can be used to generate variants in the regulatory and/or structural elements of genes in the carotenoid synthesis pathway, allowing increased expression in heterologous hosts. Indeed, traditional techniques have been used to increase carotenoid production by increasing expression of a rate limiting enzyme in *Thermus thermophilus* (Hoshino et al. *Appl. Environ. Micro.* 59:3150–3153 (1993)). Furthermore, mutation of regulatory genes can cause constitutive expression of carotenoid synthesis in actinomycetes, where carotenoid photoinducibility is otherwise unstable and lost at a relatively high frequency in some species (Kato et al. *Mol. Gen. Genet.* 247:387–390 (1995)). These are both mutations that can be obtained by recursive sequence recombination.

The recursive sequence recombination techniques of the invention as described above can be used to evolve one or more carotenoid synthesis genes in a desired host without the need for analysis of regulatory mechanisms. Since carotenoids are colored, a calorimetric assay in microtiter plates, or even on growth media plates, can be used for screening for increased production.

In addition to increasing expression of carotenoids, carotenogenic biosynthetic pathways have the potential to produce a wide diversity of carotenoids, as the enzymes involved appear to be specific for the type of reaction they will catalyze, but not for the substrate that they modify. For example, two enzymes from the marine bacterium *Agrobacterium aurantiacum* (CrtW and CrtZ) synthesize six different ketocarotenoids from $\beta$-carotene (Misawa et al. *J. Bact.* 177:6576–6584 (1995)). This relaxed substrate specificity means that a diversity of substrates can be transformed into an even greater diversity of products. Introduction of foreign carotenoid genes into a cell can lead to novel and functional carotenoid-protein complexes, for example in photosynthetic complexes (Hunter et al. *J.Bact.* 176:3692–3697 (1994)). Thus, the deliberate recombination of enzymes through the recursive sequence recombination techniques of the invention is likely to generate novel compounds. Screening for such compounds can be accomplished, for example, by the cell competition/survival techniques discussed above and by a calorimetric assay for pigmented compounds.

Another method of identifying new compounds is to use standard analytical techniques such as mass spectroscopy, nuclear magnetic resonance, high performance liquid chromatography, etc. Recombinant microorganisms can be pooled and extracts or media supernatants assayed from these pools. Any positive pool can then be subdivided and the procedure repeated until the single positive is identified ("sib-selection").

H. Indigo Biosynthesis

Many dyes, i.e. agents for imparting color, are specialty chemicals with significant markets. As an example, indigo is currently produced chemically. However, nine genes have been combined in *E. coli* to allow the synthesis of indigo from glucose via the tryptophan/indole pathway (Murdock et al. *Bio/Technology* 11:381–386 (1993)). A number of manipulations were performed to optimize indigo synthesis: cloning of nine genes, modification of the fermentation medium and directed changes in two operons to increase reaction rates and catalytic activities of several enzymes. Nevertheless, bacterially produced indigo is not currently an economic proposition. The recursive sequence recombination techniques of the instant invention could be used to optimize indigo synthesizing enzyme expression levels and catalytic activities, leading to increased indigo production, thereby making the process commercially viable and reducing the environmental impact of indigo manufacture. Screening for increased indigo production can be done by calorimetric assays of cultures in microtiter plates.

I. Amino Acids

Amino acids of particular commercial importance include but are not limited to phenylalanine, monosodium glutamate, glycine, lysine, threonine, tryptophan and methionine. Backman et al. (*Ann. NY Acad. Sci.* 589:16–24 (1990)) disclosed the enhanced production of phenylalanine in *E. coli* via a systematic and downstream strategy covering organism selection, optimization of biosynthetic capacity, and development of fermentation and recovery processes.

As described in Simpson et al. (*Biochem Soc Trans*, 23:381–387 (1995)), current work in the field of amino acid production is focused on understanding the regulation of these pathways in great molecular detail. The recursive sequence recombination techniques of the instant invention would obviate the need for this analysis to obtain bacterial strains with higher secreted amino acid yields. Amino acid production could be optimized for expression using recursive sequence recombination of the amino acid synthesis and secretion genes as well as enzymes at the regulatory phosphoenolpyruvate branchpoint, from such organisms as *Serratia marcescens*, Bacillus, and the Corynebacterium-Brevibacterium group. In some embodiments of the invention, screening for enhanced production is preferably done in microtiter wells, using chemical tests well known in the art that are specific for the desired amino acid. Screening/selection for amino acid synthesis can also be done by using auxotrophic reporter cells that are themselves unable to synthesize the amino acid in question. If these reporter cells also produce a compound that stimulates the growth of the amino acid producer (this could be a growth factor, or even a different amino acid), then library cells that produce more amino acid will in turn receive more growth stimulant and will therefore grow more rapidly.

J. Vitamin C synthesis

L-Ascorbic acid (vitamin C) is a commercially important vitamin with a world production of over 35,000 tons in 1984. Most vitamin C is currently manufactured chemically by the Reichstein process, although recently bacteria have been engineered that are able to transform glucose to 2,5-ketogluconic acid, and that product to 2-keto-L-idonic acid, the precursor to L-ascorbic acid (Boudrant, *Enzyme Microb. Technol.* 12:322–329 (1990)).

The efficiencies of these enzymatic steps in bacteria are currently low. Using the recursive sequence recombination techniques of the instant invention, the genes can be genetically engineered to create one or more operons followed by expression optimization of such a hybrid L-ascorbic acid synthetic pathway to result in commercially viable microbial vitamin C biosynthesis. In some embodiments, screening for enhanced L-ascorbic acid production is preferably done in microtiter plates, using assays well known in the art.

VI. Modification of Cell Properties.

Although not strictly examples of manipulation of intermediary metabolism, recursive sequence recombination techniques can be used to improve or alter other aspects of cell properties, from growth rate to ability to secrete certain desired compounds to ability to tolerate increased temperature or other environmental stresses. Some examples of traits engineered by traditional methods include expression of heterologous proteins in bacteria, yeast, and other eukaryotic cells, antibiotic resistance, and phage resistance. Any of these traits is advantageously evolved by the recursive sequence recombination techniques of the instant invention. Examples include replacement of one nutrient uptake system (e.g. ammonia in *Methylophilus methylotrophus*) with another that is more energy efficient; expression of haemoglobin to improve growth under conditions of limiting oxygen; redirection of toxic metabolic end products to less toxic compounds; expression of genes conferring tolerance to salt, drought and toxic compounds and resistance to pathogens, antibiotics and bacteriophage, reviewed in Cameron et. al. *Appl Biochem Biotechnol*, 38:105–140 (1993).

The heterologous genes encoding these functions all have the potential for further optimization in their new hosts by existing recursive sequence recombination technology. Since these functions increase cell growth rates under the desired growth conditions, optimization of the genes by evolution simply involves recombining the DNA recursively and selecting the recombinants that grow faster with limiting oxygen, higher toxic compound concentration, or whatever is the appropriate growth condition for the parameter being improved.

Since these functions increase cell growth rates under the desired growth conditions, optimization of the genes by "evolution" can simply involve "shuffling" the DNA and selecting the recombinants that grow faster with limiting oxygen, higher toxic compound concentration or whatever restrictive condition is being overcome.

Cultured mammalian cells also require essential amino acids to be present in the growth medium. This requirement could also be circumvented by expression of heterologous metabolic pathways that synthesize these amino acids (Rees et al. *Biotechnology* 8:629–633 (1990). Recursive sequence recombination would provide a mechanism for optimizing the expression of these genes in mammalian cells. Once again, a preferred selection would be for cells that can grow in the absence of added amino acids.

Yet another candidate for improvement through the techniques of the invention is symbiotic nitrogen fixation. Genes involved in nodulation (nod, ndv), nitrogen reduction (nif, fix), host range determination (nod, hsp), bacteriocin production (tfx), surface polysaccharide synthesis (exo) and energy utilization (dct, hup) which have been identified (Paau, *Biotech. Adv.* 9:173–184 (1991)).

The main function of recursive sequence recombination in this case is in improving the survival of strains that are already known to be better nitrogen fixers. These strains tend to be less good at competing with strains already present in the environment, even though they are better at nitrogen fixation. Targets for recursive sequence recombination such as nodulation and host range determination genes can be modified and selected for by their ability to grow on the new host. Similarly any bacteriocin or energy utilization genes that will improve the competitiveness of the strain will also result in greater growth rates. Selection can simply be performed by subjecting the target genes to recursive sequence recombination and forcing the inoculant to compete with wild type nitrogen fixing bacteria. The better the nitrogen fixing bacteria grow in the new host, the more copies of their recombined genes will be present for the next round of recombination. This growth rate differentiating selection is described above in detail.

VI. Biodetectors/Biosensors

Bioluminescence or fluorescence genes can be used as reporters by fusing them to specific regulatory genes (Cameron et. al. *Appl Biochem Biotechnol*, 38:105–140 (1993)). A specific example is one in which the luciferase genes luxCDABE of *Vibrio fischeri* were fused to the regulatory region of the isopropylbenzene catabolism operon from *Pseudomonas putida* RE204. Transformation of this fusion construct into *E. coli* resulted in a strain which produced light in response to a variety of hydrophobic compound such as substituted benzenes, chlorinated solvents and naphthalene (Selifonova et. al., *Appl Environ Microbiol* 62:778–783 (1996)). This type of construct is useful for the detection of pollutant levels, and has the added benefit of only measuring those pollutants that are bioavailable (and therefore potentially toxic). Other signal molecules such as jellyfish green fluorescent protein could also be fused to genetic regulatory regions that respond to chemicals in the environment. This should allow a variety of molecules to be detected by their ability to induce expression of a protein or proteins which result in light, fluorescence or some other easily detected signal.

Recursive sequence recombination can be used in several ways to modify this type of biodetection system. It can be used to increase the amplitude of the response, for example by increasing the fluorescence of the green fluorescent protein. Recursive sequence recombination could also be used to increase induced expression levels or catalytic activities of other signal-generating systems, for example of the luciferase genes.

Recursive sequence recombination can also be used to alter the specificity of biosensors. The regulatory region, and transcriptional activators that interact with this region and with the chemicals that induce transcription can also be shuffled. This should generate regulatory systems in which transcription is activated by analogues of the normal inducer, so that biodetectors for different chemicals can be developed. In this case, selection would be for constructs that are activated by the (new) specific chemical to be detected. Screening could be done simply with fluorescence (or light) activated cell sorting, since the desired improvement is in light production.

In addition to detection of environmental pollutants, biosensors can be developed that will respond to any chemical for which there are receptors, or for which receptors can be evolved by recursive sequence recombination, such as hormones, growth factors, metals and drugs. These receptors may be intracellular and direct activators of transcription, or they may be membrane bound receptors that activate transcription of the signal indirectly, for example by a phosphorylation cascade. They may also not act on transcription at all, but may produce a signal by some post-transcriptional modification of a component of the signal generating pathway. These receptors may also be generated by fusing domains responsible for binding different ligands with different signaling domains. Again, recursive sequence recombination can be used to increase the amplitude of the signal generated to optimize expression and functioning of chimeric receptors, and to alter the specificity of the chemicals detected by the receptor.

The following examples are offered by way of illustration, not by way of limitation.

EXAMPLES

I. Alteration of enzyme activity and specificity.

In this example, recursive sequence recombination techniques of the instant invention were used to expand the range of substrates efficiently hydrolyzed by *E. coli* β-galactosidase. The goal was to evolve wild type *E. coli* β-galactosidase into a fucosidase. The enzyme showed very weak activity with both p-nitrophenyl-β-D-fucopyranoside and o-nitrophenyl-β-D-fucopyranoside (estimated respectively as 80- and 160-fold less efficient than for p-nitrophenyl-β-D-galactopyranoside).

To increase the activity of *E. coli* β-galactosidase against these fucopyranoside derivatives, a lacZ gene (a 3.8 kb Hind III -BamHI fragment from plasmid pCH110, Pharmacia) encoding *E. coli* β-galactosidase was subcloned into plasmid p18SFI-BLA-SFI (Stemmer, *Nature*, 370:389–391 (1994)). The resulting plasmid, p18-lacZ, was used for recursive sequence recombination and mutant screening.

Purified plasmid p18-lacZ (4–5 μg) was used directly for DNase I fragmentation. Fragments with sizes between 50 and 200 bp were purified from a 2% agarose gel and used for reassembly PCR (Stemmer, *Nature* 370:389–391 (1994)). Assembly reactions used Tth polymerase (Perkin Elmer) in the manufacturer's supplied buffer. The PCR program for assembly was as follows: 94° C., 2 min., then 40 cycles of 94° C. for 30 sec.; 55° C. for 3 sec.; 72° C. for 1 min. +5 sec. per cycle; then finally 72° C. for 5 min.

This reaction was diluted 100-fold into a standard PCR reaction using the 40 mer primers p50F 5'-AGCGCCCA ATACGCAAACCGCCTCTCCCCGCGCGTTGGCC-3' [SEQ ID NO: 1] and pR34 5'-CTATGCGGCATC AGAGCAGATTGTACTGAGAGTGCACCAT-3' [SEQ ID NO: 2]. This resulted in amplification of both the desired DNA band (about 4 kb in size) as well as two smaller sized products (about 600 bp and 100 bp bands). The PCR products were digested with BamHI and Hind III and the correct size product was cloned into BamHI-HindIII digested p18-lacZ. The resulting plasmid containing a pool of recombined lacZ mutants was plated out on LB plates supplemented with kanamycin and 5-bromo-4-chloro-3-indolyl-β-D-fucopyranoside (X-fuco). Plates were incubated at 37° C. for 20 hours and screened for colonies with slight blue tint, indicating hydrolysis of the X-fuco. Plasmid DNA was prepared from positive colonies and the procedure was repeated. Thus, six rounds of recursive sequence recombination produced a ten-fold increase in X-fuco hydrolysis activity.

II. Evolution of an Entire Metabolic Pathway

As an example of evolution of an entire metabolic pathway, the recursive sequence recombination techniques of the invention were used to modify a plasmid encoding resistance to mercury salts. This plasmid, as disclosed by Wang et al. (*J. Bact.* 171:83–92 (1989)) contains at least 8 genes within 13.5 kb of Bacillus DNA inserted in the cloning vector pUC9. The recursive sequence recombination protocol used for this plasmid was as follows.

Plasmid DNA (at 130 μg/ml) was digested with 0.09 U/ml DNAse in 50 mM Tris-Cl, pH 7.4, 10 mM $MnCl_2$, for 10 minutes at 25° C. DNA fragments were not size-selected, but were purified by phenol extraction and ethanol precipitation. The assembly reaction was performed using Tth polymerase (Perkin Elmer) using the manufacturer's supplied buffer, supplemented with the following: 7.5% polyethylene glycol, 8000 MW; 35 mM tetramethylammonium chloride; and 4

U/ml Pwo(Boehringer Mannheim), Pfu(Stratagene), Vent (New England Biolabs), Deep Vent (New England Biolabs), Tfl (Promega) or Tli (Promega) thermostable DNA polymerases. DNA fragments were used at around 10 μg/ml.

The PCR program for assembly was as follows: 94° C. for 20 sec., then 40 cycles of 94° C. for 15 sec., 40° C. for 30 sec., 72° C. for 30 sec. +2 sec./cycle, and finally 72° C. for 10 min.

The recombinant plasmid was then amplified in three fragments by using primers flanking the three relatively evenly spaced AlwNI restriction sites contained in the plasmid. The sequences of these primers were:

1) 5'-CAGGACTTATCGCCACTGGCAGC-3' [SEQ ID NO: 3]
2) 5'-CTCGCTCTGCTAATCCTGTTACC-3' [SEQ ID NO: 4]
3) 5'-GCATATTATGAGCGTTTAGGCTTAATTCC-3' [SEQ ID NO: 5]
4) 5'-CGGTATCCTTTTTCCGTACGTTC-3' [SEQ ID NO: 6]
5) 5'-GTTGAAGAGGTGAAGAAAGTTCTCC-3' [SEQ ID NO: 7]
6) 5'-GTTCGTCGATTTCCACGCTTGGC-3' [SEQ ID NO: 9].

Three fragments were amplified using primers 1+4 (6 kb fragment), 2+5 (4 kb fragment) and 3+6 (6 kb fragment). These were then digested with AlwNI, gel purified and ligated together. As AlwNI is a non-palindromic cutter, the plasmid could only reassemble in the correct (original) order. The resultant plasmids were transformed into *E. coli* strain DH1OB (Gibco BRL) and selected on nutrient agar containing ampicillin 50 μg/ml and increasing concentrations of mercuric chloride (100 μM to 1000 μM) or phenylmercuric acetate (50 μM to 400 μM) Thus, in 2 rounds of recursive sequence recombination the tolerance of *E. coli* to these compounds increased by a factor of 10 (from about 100 to about 1,000 μM).

III. Recursive sequence Recombination of a Family of Related Enzymes

In this example nucleotide sequences were recombined between four homologous β-lactamases from *C. freundii, E. cloacae, K. pneumonia*, and *Y. enterocolitica*. The four genes were synthesized from oligonucleotides as described in Stemmer, et al. *Gene* 164:49–53 (1995). Briefly, the entire coding sequences of the genes were synthesized as overlapping 50-mer oligonucleotides on a commercial oligonucleotide synthesizer. The oligonucleotides were then assembled into full length genes by a standard recursive sequence recombination reaction, followed by amplification using primers common to all four genes. Oligonucleotides were designed to give optimal *E. coli* codon usage in the synthetic genes with the goal of increasing the homology to increase the frequency of recombination, and the same 5' and 3' terminal sequences. After assembly of the genes and selection for active clones, which is optional, they were DNase treated to produce fragments from 50 to 200 bp in length. The fragments were dissolved at 100 μg/ml in 15 μl of Klenow (DNA polymerase I large fragment) buffer (New England Biolabs) and subjected to manual PCR as follows: 15 cycles of 95° C. for 1 min.; freeze on dry ice and ethanol; warm to 25° C. and add 2 μl of Klenow (1 U/μl) in Klenow buffer; incubate for 2 min at 25° C.

A 5 μl aliquot of the manual PCR reaction was then diluted 6-fold into a standard Taq reaction mix (without oligonucleotide primers) and assembled using a standard PCR program consisting of 30 cycles of 94° C. for 30 sec., 40° C. for 30 sec., and 72° C. for 30 sec.

A 4, 8 or 16 μl aliquot of this second PCR reaction was then diluted into a standard Taq reaction mix containing oligonucleotide primers that prime on sequences contained in all four β-lactamase genes 5'-AGGGCCTCGTGATACGCCTATT-3' [SEQ ID NO: 9] and 5'-ACGAAAACTCACGTTAAGGGATT-3' [SEQ ID NO: 10]. Full-length product was amplified using a standard PCR program consisting of 25 cycles of 94° C. for 30 sec., 45° C. for 30 sec., 72° C. for 45 sec.

This procedure produced hybrid β-lactamase genes whose activities can be tested against antibiotics including but not limited to ampicillin, carbenicillin, cefotaxime, cefoxitine, cloxacillin, ceftazidime, cephaloridine and moxalactam, to determine the specificities of the hybrid enzymes so created. Moxalactam was chosen as the test antibiotic for hybrid genes. The best of the original β-lactamase genes used in this study conferred resistance to 0.125 μg/ml of moxalactam. After the first round of recursive sequence recombination hybrid genes were isolated that conferred resistance to 0.5 μg/ml moxalactam, yielding a 4-fold increase.

Although the foregoing invention has been described in some detail by way of illustration and example for purposes of clarity of understanding, it will be obvious that certain changes and modifications may be practiced within the scope of the appended claims.

All references cited herein are expressly incorporated in their entirety for all purposes.

What is claimed is:

1. A method of evolving a biocatalytic activity of a cell, comprising:
   (a) recombining at least a first and second DNA segment from at least one gene conferring ability to catalyze a reaction of interest, the segments differing from each other in at least two nucleotides, to produce a library of recombinant genes;
   (b) screening the library to identify at least one recombinant gene from the library that confers enhanced ability to catalyze the reaction of interest by the cell relative to a wildtype form of the gene;
   (c) recombining at least a segment from the at least one recombinant gene with a further DNA segment from the at least one gene, the same or different from said first and second DNA segments, to produce a second library of recombinant genes;
   (d) screening the second library of recombinant genes to identify at least one further recombinant gene from the second library of recombinant genes that confers enhanced ability to catalyze the reaction of interest by the cell relative to a previous recombinant gene;
   (e) repeating (c) and (d), as necessary, until the further recombinant gene confers a desired level of enhanced ability to catalyze the reaction of interest by the cell, wherein the reaction of interest is the ability to utilize a substrate as a nutrient source.

2. A method of evolving a biocatalytic activity of a cell, comprising:
   (a) recombining at least a first and second DNA segment from at least one gene conferring ability to catalyze a reaction of interest, the segments differing from each other in at least two nucleotides, to produce a library of recombinant genes;
   (b) screening the library to identify at least one recombinant gene from the library that confers enhanced ability to catalyze the reaction of interest by cell relative to a wildtype form of the gene;

(c) recombining at least a segment from the at least one recombinant gene with a further DNA segment from the at least one gene, the same or different from said first and second DNA segments, to produce a second library of recombinant genes;

(d) screening the second library of recombinant genes to identify at least one further recombinant gene from the second library of recombinant genes that confers enhanced ability to catalyze the reaction of interest by the cell relative to a previous recombinant gene;

(e) repeating (c) and (d), as necessary, until the further recombinant gene confers a desired level of enhanced ability to catalyze the reaction of interest by the cell, wherein the reaction of interest is the ability to detoxify a compound.

3. A method of evolving a biocatalytic activity of a cell, comprising:

(a) recombining at least a first and second DNA segment from at least one gene conferring ability to catalyze a reaction of interest, the segments differing from each other in at least two nucleotides, to produce a library of recombinant genes;

(b) screening the library to identify at least one recombinant gene from the library that confers enhanced ability to catalyze the reaction of interest by the cell relative to a wildtype form of the gene;

(c) recombining at least a segment from the at least one recombinant gene with a further DNA segment from the at least one gene, the same or different from said first and second DNA segments, to produce a second library of recombinant genes;

(d) screening the second library of recombinant genes to identify at least one further recombinant gene from the second library of recombinant genes that confers enhanced ability to catalyze the reaction of interest by the cell relative to a previous recombinant gene;

(e) repeating (c) and (d), as necessary, until the further recombinant gene confers a desired level of enhanced ability to catalyze the reaction of interest by the cell wherein the reaction of interest is the ability to synthesize a compound of interest and wherein the compound of interest is selected from the group consisting of an amino acid, a polymer, vitamin C, and indigo.

4. The method of claim 1, 2 or 3, wherein at least one recombining step is performed in vitro, and the resulting library of recombinants is introduced into the cell whose biocatalytic activity is to be enhanced generating a library of cells containing different recombinants.

5. The method of claim 4, wherein the in vitro recombining step comprises:

cleaving the first and second segments into fragments;

mixing and denaturing the fragments; and incubating the denatured fragments with a polymerase under conditions which result in annealing of the denatured fragments and formation of the library of recombinant genes.

6. The method of claim 1, 2 or 3, wherein at least one recombining step is performed in vivo.

7. The method of claim 1, 2 or 3, wherein at least one recombining step is performed in the cell whose biocatalytic activity is to be enhanced.

8. The method of claim 1, 2 or 3, wherein at least one DNA segment comprises a cluster of genes collectively conferring ability to catalyze a reaction of interest.

9. A method of generating a new biocatalytic activity in a cell, comprising:

(a) recombining at least first and second DNA segments from at least one gene conferring ability to catalyze a first enzymatic reaction related to a second enzymatic reaction of interest, the segments differing from each other in at least two nucleotides, to produce a library of recombinant genes;

(b) screening at least one recombinant gene from the library that confers a new ability to catalyze the second reaction of interest;

(c) recombining at least a segment from at least one recombinant gene with a further DNA segment from the at least one gene, the same or different from the first and second segments, to produce a further library of recombinant genes;

(d) screening at least one further recombinant gene from the further library of recombinant genes that confers enhanced ability to catalyze the second reaction of interest in the cell relative to a previous recombinant gene;

(e) repeating (c) and (d), as necessary, until the further recombinant gene confers a desired level of enhanced ability to catalyze the second reaction of interest in the cell.

10. A method of optimizing expression of a gene product, the method comprising:

(a) recombining at least a first and second DNA segments from at least one gene conferring ability to produce the gene product, the segments differing from each other in at least two nucleotides, to produce a library of recombinant genes;

(b) screening the library to identify at least one recombinant gene from the library that confers optimized expression of the gene product relative to a wildtype form of the gene;

(c) recombining at least a segment from the at least one recombinant gene with a further DNA segment from the at least one gene, the same or different from said first and second DNA segments, to produce a second library of recombinant genes;

(d) screening the second library of recombinant genes to identify at least one further recombinant gene from the second library of recombinant genes that confers optimized ability to produce the gene product relative to a previous recombinant gene;

(e) repeating (c) and (d), as necessary, until the further recombinant gene confers a desired level of optimized ability to express the gene product wherein at least one recombining step is performed in vivo.

11. The method of claim 10, wherein the recombining step is performed in a host cell wherein the gene product is expressed.

12. The method of claim 10, wherein the at least one gene is a host cell gene and wherein the host cell gene does not encode the gene product.

13. The method of claim 10, wherein optimization results in increased expression of the gene product.

14. A method of evolving a biosensor for a compound A of interest, the method comprising:

(a) recombining at least first and second DNA segments from at least one gene conferring ability to detect a structurally related compound B, the segments differing from each other in at least two nucleotides, to produce a library of recombinant genes;

(b) screening at least one recombinant gene from the library that confers optimized ability to detect compound A relative to a wildtype form of the gene;

(c) recombining at least a segment from the at least one recombinant gene with a further DNA segment from the at least one gene, the same or different from the first and second segments, to produce a further library of recombinant genes;

(d) screening at least one further recombinant gene from the further library of recombinant genes that confers optimized ability to detect compound A relative to a previous recombinant gene;

(e) repeating (c) and (d), as necessary, until the further recombinant gene confers a desired level of optimized ability to detect compound A.

15. The method of claim 14, wherein optimization results in increased amplitude of response by the biosensor.

16. The method of claim 14, wherein compound A and compound B are different.

17. The method of claim 14, wherein compound A and compound B are identical.

18. The method of claim 2, wherein the compound is selected from the group consisting of benzene, biphenyl, xylene, toluene, camphor, naphthalene, halogenated hydrocarbons, polychlorinated biphenyls, polycyclic aromatic hydrocarbons, trichlorethylene, pesticides, and herbicides.

19. The method of claim 18, wherein the compound is atrazine.

20. A method of evolving a biocatalytic activity of a cell, comprising:

(a) recombining at least a first and second DNA segment from at least one gene conferring ability of a dioxygenase to catalyze a reaction of interest, the segments differing from each other in at least two nucleotides, to produce a library of recombinant genes;

(b) screening the library to identify at least one recombinant gene from the library that confers enhanced ability to catalyze the reaction of interest by the cell relative to a wildtype form of the gene;

(c) recombining at least a segment from the at least one recombinant gene with a further DNA segment from the at least one gene, the same or different from said first and second DNA segments, to produce a second library of recombinant genes;

(d) screening the second library of recombinant genes to identify at least one further recombinant gene from the second library of recombinant genes that confers enhanced ability to catalyze the reaction of interest by the cell relative to a previous recombinant gene;

(e) repeating (c) and (d), as necessary, until the further recombinant gene confers a desired level of enhanced ability to catalyze the reaction of interest by the cell.

21. The method of claim 20, wherein the dioxygenase is from a Pseudomonas species.

22. A method of evolving a biocatalytic activity of a cell, comprising:

(a) recombining at least a first and second DNA segment from at least one gene conferring to the cell the ability to be resistant to a heavy metal, the segments differing from each other in at least two nucleotides, to produce a library of recombinant genes;

(b) screening the library to identify at least one recombinant gene from the library that confers enhanced ability to catalyze the reaction of interest by the cell relative to a wildtype form of the gene;

(c) recombining at least a segment from the at least one recombinant gene with a further DNA segment from the at least one gene, the same or different from said first and second DNA segments, to produce a second library of recombinant genes;

(d) screening the second library of recombinant genes to identify at least one further recombinant gene from the second library of recombinant genes that confers enhanced ability to catalyze the reaction of interest by the cell relative to a previous recombinant gene;

(e) repeating (c) and (d), as necessary, until further recombinant gene confers a desired level of enhanced ability of resistance to the heavy metal.

23. The method of claim 22, wherein the heavy metal is selected from the group consisting of mercury, arsenate, chromate, cadmium, and silver.

24. A method of evolving a biocatalytic activity of a cell, comprising:

(a) recombining at least a first and second DNA segment from at least one gene conferring ability to catalyze a reaction of interest, the segments differing from each other in at least two nucleotides, to produce a library of recombinant genes;

(b) screening the library to identify at least one recombinant gene from the library that confers enhanced ability to catalyze the reaction of interest by the cell relative to a wildtype form of the gene;

(c) recombining at least a segment from the at least one recombinant gene with a further DNA segment from the at least one gene, the same or different from said first and second DNA segments, to produce a second library of recombinant genes;

(d) screening the second library of recombinant genes to identify at least one further recombinant gene from the second library of recombinant genes that confers enhanced ability to catalyze the reaction of interest by the cell relative to a previous recombinant gene;

(e) repeating (c) and (d), as necessary, until the further recombinant gene confers a desired level of enhanced ability to catalyze the reaction of interest by the cell, wherein the reaction of interest is the ability to biocatalyze desulfurization of oil.

25. The method of claim 24, wherein the first or second DNA segment is derived from a Rhodococcus species.

26. A method of optimizing production of a metabolite by a metabolic pathway, the method comprising:

(a) recombining at least a first and second DNA segments from at least one gene conferring ability to produce the metabolite, the segments differing from each other in at least two nucleotides, to produce a library of recombinant genes;

(b) screening the library to identify at least one recombinant gene from the library that confers optimized production of the metabolite relative to a wildtype form of the gene;

(c) recombining at least a segment from the at least one recombinant gene with a further DNA segment from the at least one gene, the same or different from said first and second DNA segments, to produce a second library of recombinant genes;

(d) screening the second library of recombinant genes to identify at least one further recombinant gene from the second library of recombinant genes that confers optimized ability to produce the metabolite relative to a previous recombinant gene;

(e) repeating (c) and (d), as necessary, until the further recombinant gene confers a desired level of optimized production of the metabolite.

27. The method of claim 26, wherein at least one recombining step is performed in vivo.

28. The method of claim 26, wherein production of the metabolite is monitored by mass spectroscopy.

29. The method of claim 1, wherein the nutrient source is selected from the group consisting of lactose, whey, galactose, mannitol, xylan, cellobiose, cellulose and sucrose.

30. The method of claim 3, wherein the step of screening the library further comprises detecting the compound of interest by mass spectroscopy.

31. The method of claim 3, wherein the reaction of interest is the ability of an enzyme to synthesize the compound of interest.

32. The method of claim 6, wherein at least one recombining step is performed in the cell whose biocatalytic activity is to be enhanced.

33. A method of evolving a biocatalytic activity of a cell, comprising:

(a) recombining at least a first and second DNA segment from at least one gene conferring ability to catalyze a reaction of interest, the segments differing from each other in at least two nucleotides, to produce a library of recombinant genes;

(b) screening the library to identify at least one recombinant gene from the library that confers enhanced ability to catalyze the reaction of interest by the cell relative to a wildtype form of the gene;

(c) recombining at least a segment from the at least one recombinant gene with a further DNA segment from the at least one gene, the same or different from said first and second DNA segments, to produce a second library of recombinant genes;

(d) screening the second library of recombinant genes to identify at least one further recombinant gene from the second library of recombinant genes that confers enhanced ability to catalyze the reaction of interest by the cell relative to a previous recombinant gene;

(e) repeating (c) and (d), as necessary, until the further recombinant gene confers a desired level of enhanced ability to catalyze the reaction of interest by the cell wherein the reaction of interest is the ability to synthesize a compound of interest and wherein the compound of interest is an isoprenoid.

34. A method of evolving a biocatalytic activity of a cell, comprising:

(a) recombining at least a first and second DNA segment from at least one gene conferring ability to catalyze a reaction of interest, the segments differing from each other in at least two nucleotides, to produce a library of recombinant genes;

(b) screening the library to identify at least one recombinant gene from the library that confers enhanced ability to catalyze the reaction of interest by the cell relative to a wildtype form of the gene;

(c) recombining at least a segment from the at least one recombinant gene with a further DNA segment from the at least one gene, the same or different from said first and second DNA segments, to produce a second library of recombinant genes;

(d) screening the second library of recombinant genes to identify at least one further recombinant gene from the second library of recombinant genes that confers enhanced ability to catalyze the reaction of interest by the cell relative to a previous recombinant gene;

(e) repeating (c) and (d), as necessary, until the further recombinant gene confers a desired level of enhanced ability to catalyze the reaction of interest by the cell wherein the reaction of interest is the ability to synthesize a compound of interest and wherein the compound of interest is a polyketide.

35. A method of evolving a biocatalytic activity of a cell, comprising:

(a) recombining at least a first and second DNA segment from at least one gene conferring ability to catalyze a reaction of interest, the segments differing from each other in at least two nucleotides, to produce a library of recombinant genes;

(b) screening the library to identify at least one recombinant gene from the library that confers enhanced ability to catalyze the reaction of interest by the cell relative to a wildtype form of the gene;

(c) recombining at least a segment from the at least one recombinant gene with a further DNA segment from the at least one gene, the same or different from said first and second DNA segments, to produce a second library of recombinant genes;

(d) screening the second library of recombinant genes to identify at least one further recombinant gene from the second library of recombinant genes that confers enhanced ability to catalyze the reaction of interest by the cell relative to a previous recombinant gene;

(e) repeating (c) and (d), as necessary, until the further recombinant gene confers a desired level of enhanced ability to catalyze the reaction of interest by the cell wherein the reaction of interest is the ability to synthesize a compound of interest and wherein the compound of interest is a carotenoid.

36. A method of evolving a biocatalytic activity of a cell, comprising:

(a) recombining at least a first and second DNA segment from at least one gene conferring ability to catalyze a reaction of interest, the segments differing from each other in at least two nucleotides, to produce a library of recombinant genes;

(b) screening the library to identify at least one recombinant gene from the library that confers enhanced ability to catalyze the reaction of interest by the cell relative to a wildtype form of the gene;

(c) recombining at least a segment from the at least one recombinant gene with a further DNA segment from the at least one gene, the same or different from said first and second DNA segments, to produce a second library of recombinant genes;

(d) screening the second library of recombinant genes to identify at least one further recombinant gene from the second library of recombinant genes that confers enhanced ability to catalyze the reaction of interest by the cell relative to a previous recombinant gene;

(e) repeating (c) and (d), as necessary, until the further recombinant gene confers a desired level of enhanced ability to catalyze the reaction of interest by the cell wherein the reaction of interest is the ability to synthesize a compound of interest and wherein the compound of interest is an antibiotic.

* * * * *

UNITED STATES PATENT AND TRADEMARK OFFICE
CERTIFICATE OF CORRECTION

PATENT NO.    : 5,837,458
DATED         : November 17, 1998
INVENTOR(S)   : Jeremy Minshull, et al.

It is certified that error appears in the above-identified patent and that said Letters Patent is hereby corrected as shown below:

Title page,
Item [63] Related U.S. Application Data should read:

-- Continuation-in-part of Serial No. 621,430, Mar. 25, 1996 (abandoned), and of Serial No. 621,859, Mar. 25, 1996, and of Serial No. 537,874, March 4, 1996 (U.S. National Phase of PCT/US95/02126 Feb. 17, 1995), and of Serial No. 198,431, Feb. 17, 1994 (U.S. Patent 5,605,793). --

Column 1,
Line 5, paragraph should read as follows:
-- This application is a continuation-in-part of U.S. patent application Serial No. 08/621,430 filed March 25, 1996 (abandoned) and of Serial No. 08/621,859 filed March 25, 1996, and of Serial No. 08/537,874 filed March 4, 1996 (U.S. National Phase of PCT/US95/02126 filed February 17, 1995) and of Serial No. 08/198,431 filed February 17, 1994, now U.S. Patent No. 5,605,793, the specifications of which are incorporated herein by reference in their entirety for all purposes. --

Signed and Sealed this

Thirtieth Day of October, 2001

*Attest:*

NICHOLAS P. GODICI
*Attesting Officer*  *Acting Director of the United States Patent and Trademark Office*